United States Patent
Lee et al.

(10) Patent No.: US 10,407,388 B2
(45) Date of Patent: Sep. 10, 2019

(54) THIOUREA DERIVATIVES AS ACTIVATORS OF RORα AND PHARMACEUTICAL COMPOSITION CONTAINING SAME

(75) Inventors: Mi Ock Lee, Seoul (KR); Hyeung Geun Park, Seoul (KR); Eun Jin Kim, Seoul (KR); Ho Young Son, Seoul (KR); Hyo Jun Jung, Daejeon (KR); Suck Chang Hong, Nonsan-si (KR); Tae Young Na, Seoul (KR)

(73) Assignee: SEOUL NATIONAL UNIVERSITY R & DB FOUNDATION, Seoul (KR)

( * ) Notice: Subject to any disclaimer, the term of this patent is extended or adjusted under 35 U.S.C. 154(b) by 1690 days.

(21) Appl. No.: 15/759,588

(22) PCT Filed: May 23, 2012

(86) PCT No.: PCT/KR2012/004081
§ 371 (c)(1),
(2), (4) Date: Mar. 13, 2018

(87) PCT Pub. No.: WO2012/161518
PCT Pub. Date: Nov. 29, 2012

(65) Prior Publication Data
US 2018/0265462 A1    Sep. 20, 2018

(30) Foreign Application Priority Data

May 23, 2011  (KR) .................. 10-2011-0048455
Dec. 5, 2011  (KR) .................. 10-2011-0128903
May 23, 2012  (KR) .................. 10-2012-0054540

(51) Int. Cl.
| C07C 335/12 | (2006.01) |
| A61P 9/10 | (2006.01) |
| A61P 1/16 | (2006.01) |
| A61P 3/06 | (2006.01) |
| A61P 29/00 | (2006.01) |

(52) U.S. Cl.
CPC .............. *C07C 335/12* (2013.01); *A61P 1/16* (2018.01); *A61P 3/06* (2018.01); *A61P 9/10* (2018.01); *A61P 29/00* (2018.01)

(58) Field of Classification Search
CPC .................................................. C07C 335/12
See application file for complete search history.

(56) References Cited

U.S. PATENT DOCUMENTS

| 3,090,810 | A  | 5/1963  | Berger et al.  |
| 3,949,089 | A  | 4/1976  | Maxwell et al. |
| 3,968,243 | A  | 7/1976  | Maxwell et al. |
| 2002/0147365 | A1 | 10/2002 | Abbott et al.  |
| 2008/0286231 | A1 | 11/2008 | Buchholz et al. |

OTHER PUBLICATIONS

Goldfarb, et al. Document No. 151:92845 retrieved from STN; entered in STN on Jul. 16, 2009.*
Yoon, et al. Document No. 148:562353, retrieved from STN; entered in STN on May 15, 2008.*
Kim, et al. Document No. 141:424663, retrieved from STN; entered in STN on Sep. 26, 2004.*
Wohlman, et al. Document No. 137:98670, retrieved from STN; entered in STN on Jul. 19, 2002.*
Hahn, et al. Document No. 136:36940 retrieved from STN; entered in STN on Jan. 10, 2002.*
Chen, et al. Document No. 99:87772 retrieved from STN; entered in STN on May 12, 1984.*
Vasilev, et al. Document No. 92:210085 retrieved from STN; entered in STN on May 12, 1984.*
Maxwell, et al. Document No. 76:72282 retrieved from STN; entered in STN on May 12, 1984.*
Nishie, et al. Document No. 65:59592 retrieved from STN; entered in STN on Apr. 22, 2001.*
Nitta, et al. Document No. 59:61862 retrieved from STN; entered in STN on Apr. 22, 2001.*
Berger, et al. Document No. 59:61861 retrieved from STN; entered in STN on Apr. 22, 2001.*
Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Hahn et al., "Synthesis of 2-Benzylimino-1,3-thiazolines and Their Structure Determination", Journal of the Korean Chemical Society, 2001, vol. 45, pp. 612-615.
Kim et al., "Liquid Crystalline Properties of Polyguanidines", Macromolecules, 2004, vol. 37, pp. 8286-8292.

* cited by examiner

*Primary Examiner* — Shawquia Jackson
(74) *Attorney, Agent, or Firm* — Vorys, Sater, Seymour & Pease LLP; Mih Suhn Koh

(57) ABSTRACT

Provided is a compound activating RORα gene, particularly a JC1 compound containing CGP52608 thiazolidinedione as a lead substance, and a pharmaceutically acceptable salt thereof. The compound is a lipid accumulation inhibitor and applicable to the treatment of metabolic diseases or inflammatory diseases.

10 Claims, 18 Drawing Sheets

Specification includes a Sequence Listing.

Control

Experimental group administered JC1-40

THIOUREA DERIVATIVES AS ACTIVATORS OF RORα AND PHARMACEUTICAL COMPOSITION CONTAINING SAME

STATEMENT REGARDING GOVERNMENT RIGHTS

The present invention was undertaken with the support of 1) Development of lncRNA-based new therapeutic targets for non-alcoholic fatty liver diseases No. 2017R1A2B3011870 grant funded by National Research Foundation of Korea (NRF).

SEQUENCE LISTING

The Sequence Listing submitted in text format (.txt) filed on Mar. 13, 2018, named "SequenceListing.txt", created on Feb. 27, 2018 (4.57 KB), is incorporated herein by reference.

TECHNICAL FIELD

The present invention relates to a novel thiourea derivative that activates the retinoic acid-related orphan receptor α (RORα) gene or a pharmaceutically acceptable salt thereof, and a pharmaceutical composition including the same.

BACKGROUND ART

RORα (also known as NR1F1, RORA or RZR) is a member of the steroid hormone receptor superfamily, and is a transcriptional factor that regulates gene expression. RORα consists of an N-terminal transactivation domain, a DNA-binding domain, and a C-terminal ligand-binding domain. RORα binds to ROR-binding response elements (ROREs) in the promoter of target genes, and RORE contains hexanucleotide motifs (5-AGGTCA-3') and A/T rich sequences of 6 base pairs preceding the hexanucleotide (Jetten A M et al., (2001) Prog Nucleic Acid Res Mol Biol. 69:205-47). The activity of RORα is regulated by the binding of a ligand to the C-terminal ligand-binding domain, and known ligands include cholesterol, cholesterol derivatives, melatonin, and CGP52608, which is one of thiazolidinediones (Kallen J et al., (2002) Structure. 10:1697-707/ Kallen J et al., (2004) J Biol Chem. 279:14033-8/ Wiesenberg I et al., (1995) Nucleic Acids Res. 23:327-33). It has been discovered by X-ray crystallography that cholesterol and cholesterol derivatives bind to the ligand-binding domain of RORα (Kallen J A et al., (2002) Structure. 10:1697-707/Kallen J et al., (2004) J Biol Chem. 279: 14033-8). It has also been reported that melatonin specifically binds to RORα to induce RORα-mediated gene activity regulation, and that CGP52608 is a synthetic ligand that binds to RORα competitively with melatonin (Wiesenberg I et al., (1995) Nucleic Acids Res. 23:327-33). RORα regulates genes expressing Apo A, Apo V, and Apo C III, which are apolipoproteins, thereby transferring cholesterol of the peripheral tissue to the liver for removal (Vu-Dac N et al., (1997) J Biol Chem. 272:22401-4/Lind U et al., (2005) Biochem Biophys Res Commun. 330:233-41). This suggests that RORα may be applicable to the regulation of homeostasis of cholesterol and lipid metabolism-related diseases.

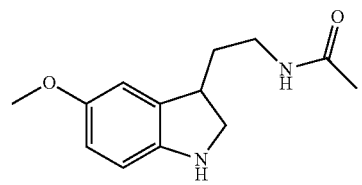

Melatonin

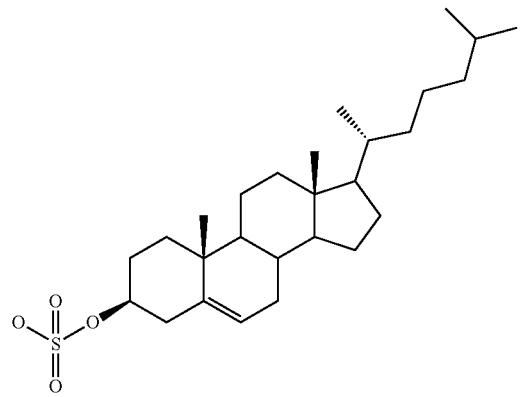

Cholestrol sulfate

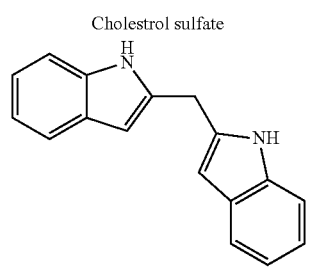

Diindolemethane

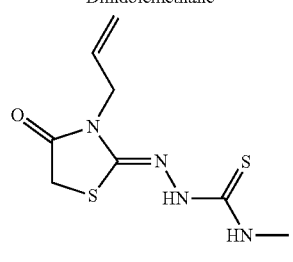

CGP52608

Liver X receptor α (LXRα) is a transcriptional factor whose activity is regulated by ligands, and is a member of the nuclear hormone receptor superfamily (Baranowski M. (2008) J Physiol Pharmacol. Suppl 7:31-55). LXRα is a vital factor in lipid and carbohydrate metabolism, and increases the expression of SREBP-1, FAS and SCD-1 genes to induce fatty acid biosynthesis in the liver (Joseph S B et al., (2002) J Biol Chem. 277:11019-25). Due to an increase in LXRα-mediated expression of these genes, the accumulation of triglycerides occurs in hepatocytes, and this causes fatty liver and hypertriglyceridemia. In other words, the expression of enzymes that induce lipid synthesis in the liver is increased by LXR activators, and this causes hyperlipoidemia and fatty acid (Schultz J R et al., (2000) Genes Dev. 14:2831-8). Among these enzymes, fatty acid synthase (FAS) is an enzyme that participates in the final stage of fatty acid biosynthesis, and is also a target gene of LXR and SREBP-1 (Clarke S D. (1993) J Anim Sci. 71:1957-65). It is known that RORα contributes to regulating genes that are vital for lipid synthesis, by crosstalk with LXR (Wada T et al., (2008) Exp Biol Med (Maywood)).

Acetyl-CoA carboxylase (ACC) is a major enzyme in the fatty acid production pathway that regulates the conversion of acetyl-CoA into malonyl-CoA (Tong L et al., (2006) J Cell Biochem. 99:1476-88). Malonyl-CoA produced by ACC inhibits CPT-1, which is an enzyme that plays a key role in inducing fatty acid oxidation in mitochondria, thereby inhibiting the oxidation of fatty acids, and ACC is inactivated and loses the ability to inhibit the oxidation of fatty acids when serine residues thereof are phosphorylated by a kinase such as AMPK (Brownsey R W et al., (2006) Biochem Soc Trans. 34:223-7).

DISCLOSURE

Technical Problem

To develop a material capable of effectively inhibiting lipid accumulation, as a result of conducting structure activity studies using CGP52608, which is an existing thiazolidinedione-based compound, as a leading substance, the inventors of the present invention synthesized novel thiourea-based compounds that exhibit selective activity against RORα. Thus, an object of the present invention is to provide a novel lipid accumulation inhibitor through synthesis of novel thiourea derivatives that exhibits activity against RORα.

However, technical objects to be achieved by the present invention are not limited to the above-described objects, and other unmentioned objects will become apparent from the following description to those of ordinary skill in the art.

Technical Solution

The present invention provides a novel compound that activates the retinoic acid-related orphan receptor α (RORα) gene or a pharmaceutically acceptable salt thereof.

The present invention also provides a lipid accumulation inhibitor including, as an active ingredient, a novel compound that activates the RORα gene or a pharmaceutically acceptable salt thereof.

The present invention also provides a pharmaceutical composition for preventing or treating a metabolic or inflammatory disease, including: a pharmaceutically effective amount of a novel compound that activates the RORα gene or a pharmaceutically acceptable salt thereof and a pharmaceutically acceptable carrier.

The disease includes arteriosclerosis, fatty liver, alcoholic fatty liver, hyperlipidemia, and the like.

The present invention also provides a method of preventing or treating a metabolic or inflammatory disease, including administering the pharmaceutical composition.

Advantageous Effects

A compound according to the present invention is expected to be effective in the treatment and prevention of metabolic diseases and inflammatory diseases through various in vivo functions of RORα, and is useful particularly for the prevention and treatment of liver diseases through the regulation of cholesterol homeostasis and the inhibition of lipid synthesis.

BEST MODE

Figure 1:
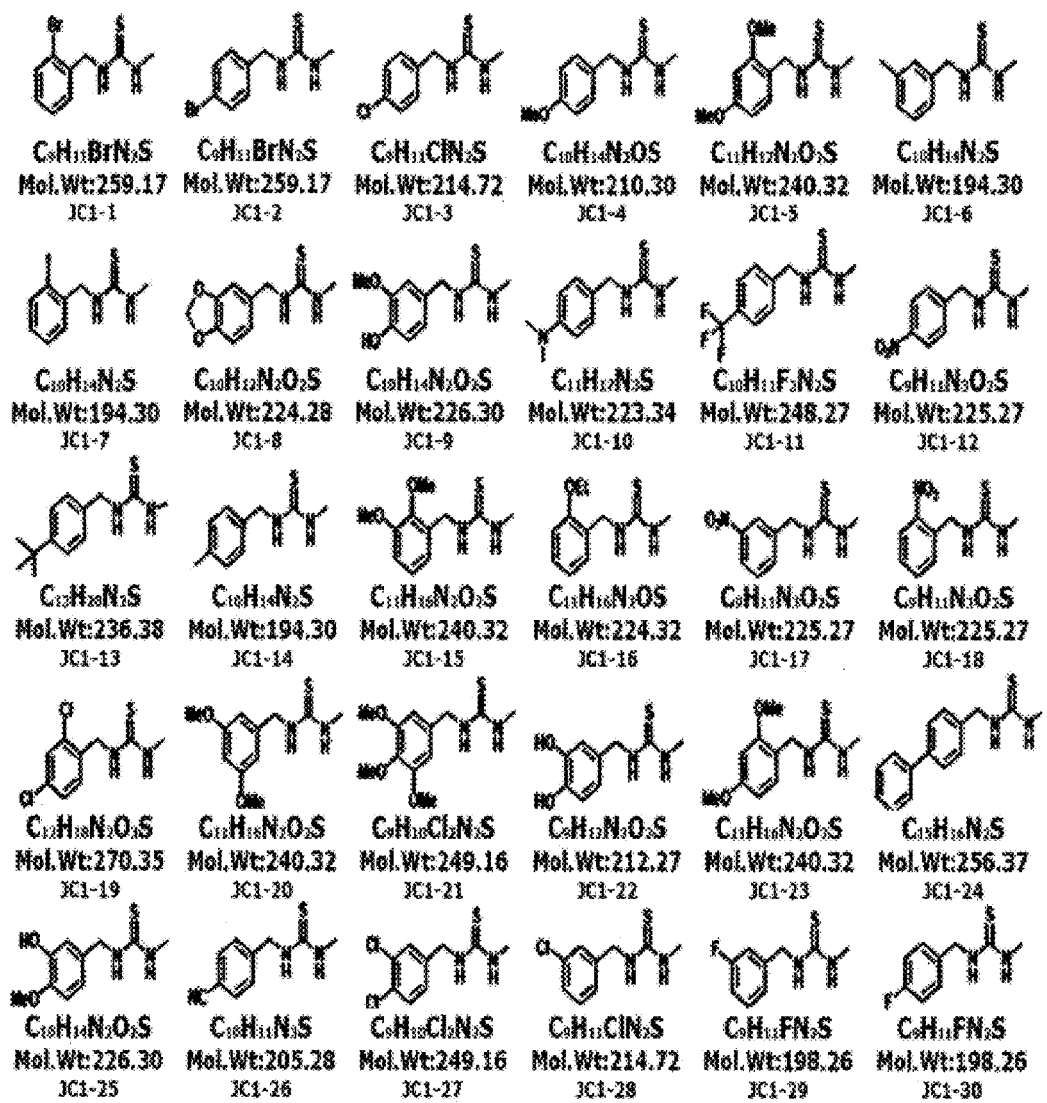
FIGS. 1 and 2 illustrate chemical structures of JC1 compounds synthesized as RORα activator candidates.
Figure 2:
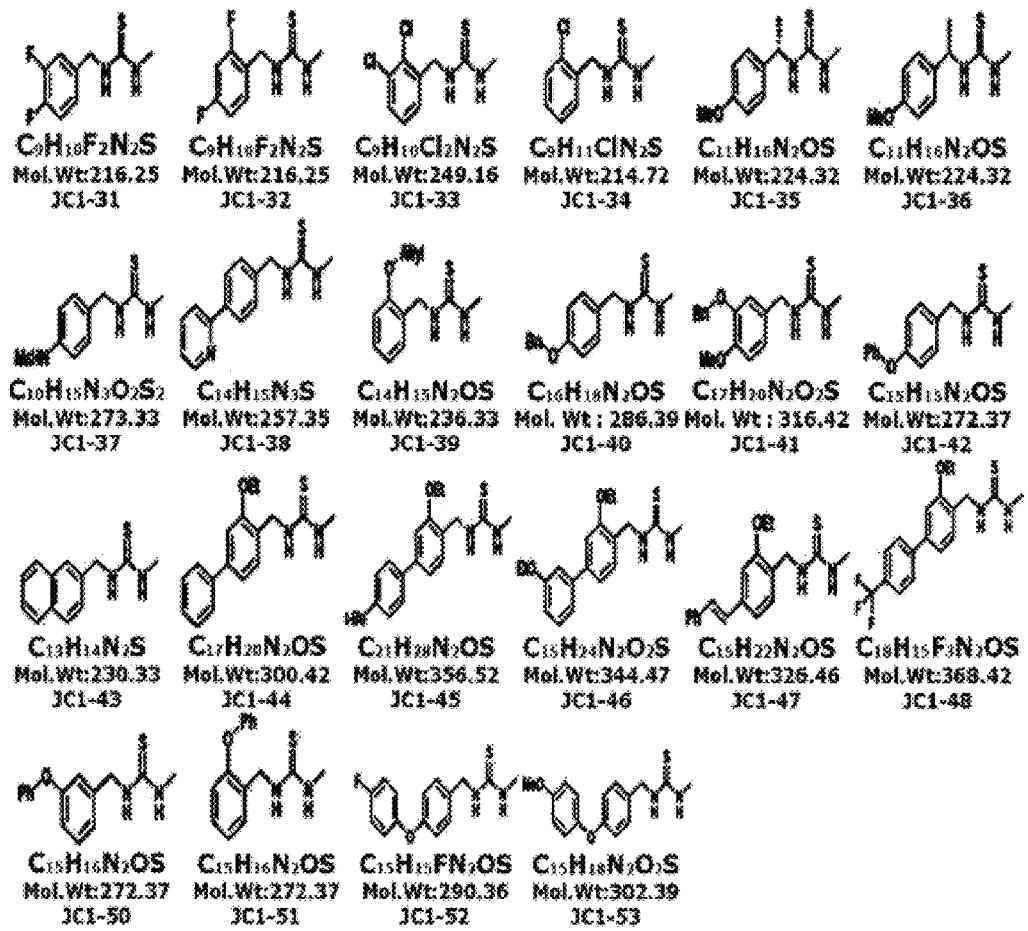

The present invention provides a novel compound that activates the retinoic acid-related orphan receptor α (RORα) gene or a pharmaceutically acceptable salt thereof. In particular, the present invention provides a lipid accumulation inhibitor that activates the expression of the RORα gene through the novel compound or a pharmaceutically acceptable salt thereof, and thus decreases the gene expression of LXRα, SREBP-1, and FAS and increases the inactivation of acetyl-CoA carboxylase (ACC), thereby inhibiting lipid synthesis in hepatocytes and inducing fatty acid oxidation to inhibit lipid accumulation. The present invention also provides a pharmaceutical composition for the prevention or treatment of a metabolic or inflammatory disease, including: a pharmaceutically effective amount of a novel compound that activates the RORα gene or a pharmaceutically acceptable salt thereof; and a pharmaceutically acceptable carrier. The present invention also provides a method of preventing or treating a metabolic or inflammatory disease, including: administering the above-described pharmaceutical composition to an individual. As used herein, the expression "activator that activates the RORα gene" refers to an activator that (a) activates the expression of the RORα gene; and/or (b) promotes the transcriptional activity of the expressed RORα protein.

It is known that the expression of enzymes that induce lipid synthesis in the liver is increased by an LXR activator, causing hyperlipoidemia and fatty liver (Schultz J R et al., (2000) Genes Dev. 14:2831-8). Among these enzymes, fatty acid synthase (FAS) is an enzyme that participates in the final stage of fatty acid biosynthesis, and is also a target gene of LXR and SREBP-1 (Clarke S D. (1993) J Anim Sci. 71:1957-65). In addition, fatty acid oxidation is as important in lipid metabolism as fatty acid biosynthesis. Acetyl-CoA carboxylase (ACC) is an enzyme that produces malonyl-CoA during fatty acid biosynthesis, and the produced malonyl-CoA inhibits the β-oxidation of fatty acids occurring in mitochondria in hepatocytes. ACC is inactivated when phosphorylated by a kinase such as AMPK (Brownsey et al., 2006). When ACC is inactivated, the ability of ACC to inhibit fatty acid oxidation is weakened.

As a result of having made intensive efforts to develop a substance capable of effectively inhibiting lipid accumulation, the inventors of the present invention discovered that an activator for activating the RORα gene could inhibit lipid accumulation in hepatocytes. That is, the inventors of the present invention observed that, when cells were infected with RORα1 virus, the expression of the LXR protein was inhibited. Thus, the inventors of the present invention discovered molecular mechanisms where, when the gene expression of RORα (also known as NR1F1, RORA or RZR), which is a member of the steroid hormone receptor superfamily of transcriptional factors that regulate gene expression, is activated, the expressed RORα decreases the transcriptional activities of the LXRα and SREBP-1 genes and decreases the gene expression of LXRα, SREBP-1, and FAS, and the inactivation of ACC is increased to inhibit lipid synthesis in hepatocytes and induce fatty acid oxidation, and eventually results in the inhibition of lipid accumulation. The present invention was completed based on these molecular mechanisms. In the present invention, the RORα gene is a target gene.

Therefore, the present invention provides a novel compound that activates the RORα gene or a pharmaceutically acceptable salt thereof.

The novel compound that activates the RORα gene is a thiourea derivative (hereinafter, referred to as a JC1 compound) using the existing thiazolidinedione-based compound CGP52608 as a leading material, and may be represented by Formula (I) below:

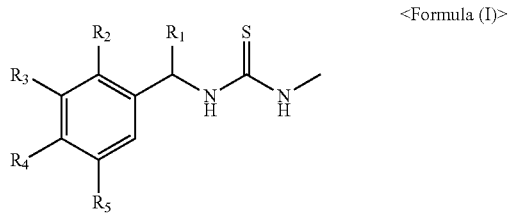

<Formula (I)> wherein, in Formula (I) above, $R_1$ may be a hydrogen atom or a $C_1$-$C_3$ alkyl group;

$R_2$ may be a hydrogen atom, a halogen atom, a $C_1$-$C_3$ alkyl group, a $C_1$-$C_3$ alkoxy group, a nitro group, a hydroxyl group, or a phenoxy group;

$R_3$ may be a hydrogen atom, a halogen atom, a $C_1$-$C_3$ alkyl group, a $C_1$-$C_3$ alkoxy group, a nitro group, a hydroxyl group, or a phenoxy group;

$R_4$ may be a hydrogen atom, a halogen atom, a $C_1$-$C_3$ alkyl group, a $C_1$-$C_3$ alkoxy group, a nitro group, a hydroxyl group, a cyano group, a dimethylamino group, a methylsulfonylamide group, a trifluoromethyl group, a vinyl benzene group, a phenoxy group, a benzoxy group, an aryl group, or a phenylamine group; and $R_5$ may be a hydrogen atom, a halogen atom, a $C_1$-$C_3$ alkyl group, a $C_1$-$C_3$ alkoxy group, a nitro group, a hydroxyl group, or a phenoxy group.

In addition, when the $R_4$ group is an aryl group or a phenoxy group, the aromatic ring may be substituted with a $C_1$-$C_3$ alkyl group, a $C_1$-$C_3$ alkoxy group, a trifluoromethyl group, or a t-butyl group.

In addition, the $R_3$ and $R_4$ groups may be linked to each other via a ring in the above-described substituents.

In addition, the $R_2$ to $R_5$ groups may be simultaneously substituted with the same or mutually different substituents.

The novel compound of the present invention may be chemically synthesized by methods shown in the following reaction schemes. These methods are provided for illustrative purposes only, and the present invention is not limited thereto.

[Reaction Scheme 1]

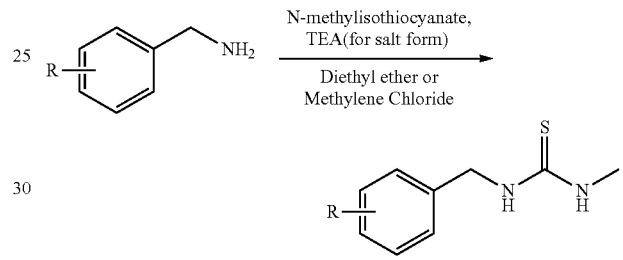

The compound of Formula (I) is synthesized as a desired thiourea nucleaus compound by coupling a substituted benzylamine-type base compound (adding dropwise trimethylamine (TEA) in the case of a salt form) with N-methylisothiocyanate in the presence of diethyl ether or methylene chloride solvent (methanol or dimethylformamide (DMF) is also used when a starting material is not dissolved).

R is a substituent of $R_2$ to $R_5$ in Formula (I) and may be a hydrogen atom, a halogen atom, a $C_1$-$C_3$ alkyl group, a $C_1$-$C_3$ alkoxy group, a nitro group, a hydroxyl group, a cyano group, a dimethylamino group, a methylsulfonylamide group, a trifluoromethyl group, a vinyl benzene group, a phenoxy group, a benzoxy group, an aryl group, or a phenylamine group; when R is an aryl group or a phenoxy group, the aromatic ring may be substituted with a $C_1$-$C_3$ alkyl group, a $C_1$-$C_3$ alkoxy group, a trifluoromethyl group, or a t-butyl group.

[Reaction Scheme 2]

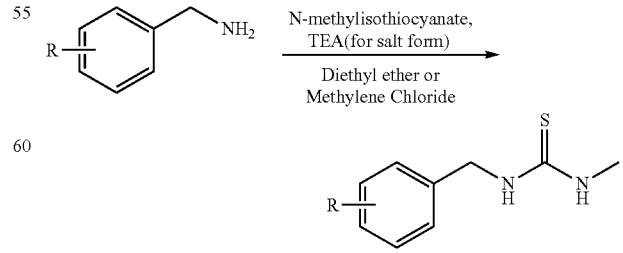

The compound of Formula (I) is synthesized as a thiourea nucleaus compound with various substituents by allowing a benzaldehyde structure to undergo a reductive amination reaction with thiourea. An intermediate is formed by reacting ti(4)-isopropoxide and N-methylthiourea with the substituted benzaldehyde structure in the presence of tetrahydrofuran (THF) solvent, and the intermediate is reacted with NaBH$_4$ to synthesize thiourea, which is a desired material.

R is the same as defined above.

[Reaction Scheme 3]

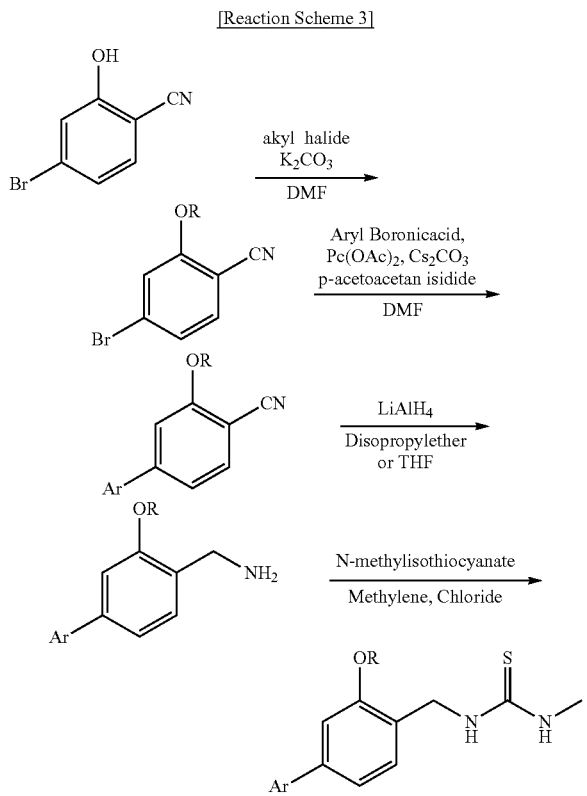

The alkylation of a hydroxyl group is performed on 5-bromo-2-cyanophenol, which is commercially available, using K$_2$CO$_3$ and an alkyl halide. In addition, a coupling reaction is performed by Suzuki coupling using Cs$_2$CO$_3$ base and an aryl boronic acid in the presence of a palladium catalyst. A cyano group at the 2-position is reduced using lithium aluminum hydride (LAH) to obtain benzylamine, and, finally, the resulting product is coupled with N-methyl isothiocyanate to thereby complete the synthesis of thiourea, which is a desired compound and represented by Formula (I).

R is a C$_1$-C$_3$ alkyl group, and

Ar, which corresponds to R$_4$ in Formula (I), is a vinyl benzene group or an aryl group; when Ar is an aryl group, the aromatic ring may be substituted with a C$_1$-C$_3$ alkyl group, a C$_1$-C$_3$ alkoxy group, a trifluoromethyl group, or a t-butyl group.

[Reaction Scheme 4]

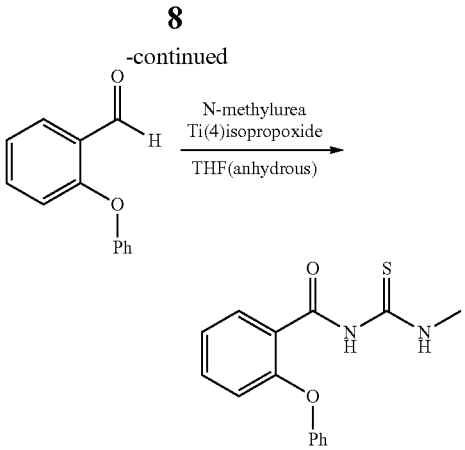

Phenol is nucleophilically added to commercially available 2-fluorobenzaldehyde used as a starting material, and the resulting substrate is subjected to reductive amination as in Reaction Scheme 2, thereby completing the synthesis of thiourea.

The present invention also provides a lipid accumulation inhibitor that activates the expression of the RORα gene through the novel compound represented by Formula (I), which activates the RORα gene, or a pharmaceutically acceptable salt thereof, and thus decreases the gene expression of LXRα, SREBP-1, and FAS and increases the inactivation of acetyl-CoA carboxylase (ACC), thereby inhibiting lipid synthesis in hepatocytes and inducing fatty acid oxidation to inhibit lipid accumulation.

The present invention also provides a pharmaceutical composition for the prevention or treatment of a metabolic or inflammatory disease, including a pharmaceutically effective amount of a novel compound of Formula (I), which activates the RORα gene, or a pharmaceutically acceptable salt thereof, a pharmaceutically acceptable carrier, and an adjuvant or a diluted solution. The pharmaceutical composition according to the present invention is expected to be effective in the treatment and prevention of metabolic diseases and inflammatory diseases, and it may be used particularly to prevent or treat a liver disease through the regulation of cholesterol homeostasis and the inhibition of lipid synthesis. Preferably, the liver disease may include fatty liver, alcoholic fatty liver, hyperlipidemia, and the like. In addition, the novel compound of the present invention, e.g., JC1 compounds, which activates the RORα gene, is expected to be applicable to the inhibition of formation of atherosclerotic plaques accompanied by vascular smooth muscle proliferation and the prevention of vascular restenosis caused by vascular smooth muscle proliferation after a balloon therapy or stenting.

The present invention also provides a method of preventing or treating a metabolic disease or an inflammatory disease, including: administering the pharmaceutical composition to an individual.

The term "individual" as used herein refers to a subject with a disease requiring treatment and, more particularly, includes mammals such as humans or non-human primates, e.g., mice, rats, dogs, cats, horses, cows, and the like. In addition, it is obvious to those of ordinary skill in the art that, in the present invention, the pharmaceutically effective amount may be variously adjusted according to body weights, ages, gender, physical conditions, and diets of patients, administration time, administration method, excretion rate, the severity of diseases, and the like.

The compounds of the present invention may be pharmaceutically administered as a pharmaceutically acceptable salt form of the compound, and the compounds of the present invention may be used alone or in combination with other pharmaceutically active compounds, or a suitable combination thereof may also be used. The salt of the compound of the present invention may be a pharmaceutically acceptable salt, and may be prepared by a currently known method, such as by adding an inorganic base, an organic base, an inorganic acid, an organic acid, or a basic or acidic amino acid to the compound according to the present invention.

The pharmaceutical composition of the present invention includes a pharmaceutically acceptable carrier. The pharmaceutically acceptable carrier may include a saline solution, polyethylene glycol, ethanol, vegetable oil, isopropyl myristate, and the like, but the present invention is not limited thereto.

The compound of the present invention may be formulated as an ointment or a cream for local application, or as an injection by dissolving, suspending, or emulsifying the compound in an aqueous solution such as a normal saline solution or 5% dextrose, or a non-aqueous solvent such as vegetable oil, a synthetic fatty acid glyceride, a higher fatty acid ester, or propylene glycol. Preparations of the present invention may include general additives, such as solubilizers, isotonic agents, suspending agents, emulsifying agents, stabilizers, and antiseptics.

A suitable dose of the compound of the present invention may vary according to conditions and body weights of patients, the severity of diseases, dosage forms, administration routes, and administration periods, and may be appropriately selected by those of ordinary skill in the art. However, preferably, the compound of the present invention is administered in an amount of 0.0001 mg/kg (body weight)/day to 100 mg/kg (body weight)/day, more preferably, 0.01 mg/kg (body weight)/day to 30 mg/kg (body weight)/day. The compound may be administered in a single dose or multiple doses daily. In the pharmaceutical composition, the compound of the present invention is included in an amount of 0.0001 wt % to 10 wt %, preferably, 0.001 wt % to 1 wt %, with respect to the total weight of the entire composition.

The pharmaceutical composition of the present invention may be administered to mammals such as mice, rats, livestock, humans, and the like via various routes. Administration methods are not limited, and examples thereof include oral administration, rectal administration, intravenous injection, intramuscular injection, subcutaneous injection, intrauterine dural injection, or intracerebroventricular injection.

In an experimental example of the present invention, it was confirmed that JC1 compounds, preferably JC1-38, JC1-40, and JC1-42 had excellent activity in the transcription of RORα (see Experimental Examples 1 and 2).

In another experimental example of the present invention, it was confirmed that the JC1 compounds decreased the transcriptional activities of LXRα and SREBP-1 (see Experimental Example 3). In still another experimental example, it was confirmed that the JC1 compounds inhibited the expression of LXRα, SREBP-1, and FAS proteins (see Experimental Example 4). In other words, it was confirmed that the JC1 compounds of the present invention regulated not only the transcriptional activities of genes including fatty acid synthesis, but also the expression of the corresponding proteins.

In yet another experimental example of the present invention, it was confirmed that the JC1 compounds accelerated the inactivation of ACC by increasing the phosphorylation of ACC, thereby increasing fatty acid oxidation (see Experimental Example 5). In another additional experimental example, it was confirmed that the JC1 compounds inhibited lipid accumulation in hepatocytes (see Experimental Example 6).

Based on the above results, it is expected that novel compounds activating the RORα gene, e.g., JC1 compounds, are applicable to the treatment of metabolic diseases or inflammatory diseases.

Hereinafter, exemplary embodiments will be described to aid in understanding of the present invention. However, these examples are provided only to promote understanding of the present invention and are not intended to limit the scope of the present invention.

EXAMPLES

Example 1. Preparation of 1-(2-bromo-benzyl)-3-methyl-thiourea (JC1-1)

As in Reaction Scheme 1, triethylamine (TEA, 0.09 ml, 0.64 mmol) was added to 2-bromobenzylamine (100 mg, 0.54 mmol) in the presence of methylene chloride solvent, and then N-methyl isothiocyanate (0.08 ml, 1.18 mmol) was added thereto, followed by stirring. Thereafter, a white solid crystal was seen to be deposited over time. After confirming by thin layer chromatography (TLC) that the base compound had disappeared, the solid was filtered off by a vacuum filter to obtain a white solid (101 mg, 0.39 mmol). (Yield: 72%)

$^1$H-NMR (300 MHz, CDCl$_3$) δ7.53 (m, 2H), 7.45 (m, 1H) 7.15 (m, 1H), 4.78 (s, 2H), 2.99 (s, 3H)

Example 2. Preparation of 1-(4-bromo-benzyl)-3-methyl-thiourea (JC1-2)

A white solid (30 mg, 0.12 mmol) was obtained in the same manner as in Example 1, but by using 4-bromobenzylamine. (Yield: 52%)

$^1$H-NMR (300 MHz, CD3OD) δ7.46-7.42 (m, 2H), 7.24-7.21 (d, J=11.1 Hz, 2H), 4.67 (s, 2H), 2.93 (s, 3H)

Example 3. Preparation of 1-(4-chloro-benzyl)-3-methyl-thiourea (JC1-3)

As in Reaction Scheme 1, N-methylisothiocyante (320 mg, 3.10 mmol) was added to 4-chlorobenzylamine (200 mg, 1.41 mmol) in the presence of diethyl ether (3 ml) solvent, followed by stirring. Thereafter, a solid crystal was seen to be deposited over time. After confirming by TLC that the base compound had disappeared, the solid was filtered off by a vacuum filter to obtain a white solid (213.6 mg, 1.00 mmol). (Yield: 71%)

$^1$H-NMR (300 MHz, CDCl$_3$) δ7.32-7.24 (m, 4H), 7.45 (m, 1H) 4.67 (m, 2H), 2.97 (m, 3H)

Example 4. Preparation of 1-(4-methoxy-benzyl)-3-methyl-thiourea (JC1-4)

A white solid (259.6 mg, 1.23 mmol) was obtained in the same manner as in Example 3, but by using 4-methoxybenzylamine. (Yield: 57%)

¹H-NMR (300 MHz, CDCl₃) δ7.20 (m, 2H), 6.86 (m, 2H) 4.55 (m, 2H), 3.77 (m, 3H), 2.94 (m, 3H)

Example 5. Preparation of 1-(2,4-dimethoxy-benzyl)-3-methyl-thiourea (JC1-5)

A white solid (122.3 mg, 0.51 mmol) was obtained in the same manner as in Example 3, but by using 2,4-dimethoxybenzylamine. (Yield: 85%)
¹H-NMR (300 MHz, CD3OD) δ7.24-7.15 (m, 1H), 6.43-6.40 (m, 2H) 4.46 (s, 2H), 3.80-3.76 (d, J=12.1 Hz, 6H), 2.93 (s, 3H)

Example 6. Preparation of 1-(3-methyl-benzyl)-3-methyl-thiourea (JC1-6)

A white solid (144 mg, 0.74 mmol) was obtained in the same manner as in Example 3, but by using 3-methylbenzylamine. (Yield: 99%)
¹H-NMR (300 MHz, CDCl₃) δ7.36 (m, 2H), 7.21 (m, 2H) 4.71 (s, 2H), 3.09 (d, 3H), 2.45 (s, 3H)

Example 7. Preparation of 1-(2-methyl-benzyl)-3-methyl-thiourea (JC1-7)

A white solid (167 mg, 1.16 mmol) was obtained in the same manner as in Example 3, but by using 2-methylbenzylamine. (Yield: 99%)
¹H-NMR (400 MHz, CD3OD) δ7.18 (m, 4H), 4.59 (s, 2H), 2.86 (s, 3H), 2.27 (s, 3H)

Example 8. Preparation of 1-(benzo[1,3]dioxyl-5-methyl)-3-methyl-thiourea (JC1-8)

A yellow solid (132 mg, 0.59 mmol) was obtained in the same manner as in Example 3, but by using benzo[1,3]dioxyl-5-methylamine. (Yield: 89%)
¹H-NMR (300 MHz, DMSO) δ7.13-6.75 (m, 3H), 5.97 (s, 2H), 4.53 (s, 2H), 2.50 (s, 3H)

Example 9. Preparation of 1-(4-hydroxy-3-methoxy-benzyl)-3-methyl-thiourea (JC1-9)

A white solid (953 mg, 4.21 mmol) was obtained in the same manner as in Example 1, but by using 4-hydroxy-3-methoxybenzylamine. (Yield: 80%)
¹H-NMR (300 MHz, DMSO) δ8.85 (s, 1H), 6.90 (s, 1H) 6.70 (s, 1H), 4.50 (s, 2H), 3.74 (s, 3H) 2.83 (s, 3H)

Example 10. Preparation of 1-(4-dimethylamino-benzyl)-3-methyl-thiourea (JC1-10)

A yellow solid (352 mg, 1.58 mmol) was obtained in the same manner as in Example 1, but by using 4-dimethylaminobenzylamine. (Yield: 47%)
¹H-NMR (400 MHz, DMSO) δ7.13 (m, 2H), 6.68 (m, 2H), 4.48 (s, 2H), 2.85 (m, 9H)

Example 11. Preparation of 1-(4-trifluoromethyl-benzyl)-3-methyl-thiourea (JC1-11)

A yellow solid (82 mg, 0.36 mmol) was obtained in the same manner as in Example 3, but by using 4-trifluoromethylbenzylamine. (Yield: 55%)
¹H-NMR (400 MHz, CDCl₃) δ7.61-7.28 (d, J=8.3 Hz, 2H), 6.68 (d, J=8.0 Hz 2H), 4.82-4.80 (d, J=5.0 Hz, 2H), 2.98-2.97 (d, J=5.0 Hz 3H)

Example 12. Preparation of 1-(4-nitro-benzyl)-3-methyl-thiourea (JC1-12)

A yellow solid (132 mg, 0.59 mmol) was obtained in the same manner as in Example 1, but by using 4-nitrobenzylamine. (Yield: 89%)
¹H-NMR (300 MHz, DMSO) δ8.20-8.17 (d, J=8.4 Hz, 2H), 7.53-7.50 (d, J=8.4 Hz 2H), 4.79 (s, 2H), 2.83 (s, 3H)

Example 13. Preparation of 1-(4-t-butyl-benzyl)-3-methyl-thiourea (JC1-13)

A white solid (144 mg, 0.61 mmol) was obtained in the same manner as in Example 3, but by using 4-t-butylbenzylamine. (Yield: 99%)
¹H-NMR (300 MHz, DMSO) δ7.38-7.35 (d, J=8.2 Hz, 2H), 7.53-7.50 (d, J=8.1 Hz, 2H), 4.61 (s, 2H), 2.97-2.96 (d, J=4.6 Hz, 3H), 1.3 (s, 9H)

Example 14. Preparation of 1-(4-methyl-benzyl)-3-methyl-thiourea (JC1-14)

A white solid (110 mg, 0.57 mmol) was obtained in the same manner as in Example 3, but by using 4-methylbenzylamine. (Yield: 69%)
¹H-NMR (300 MHz, CDCl₃) δ7.29-7.21 (m, 4H), 4.67 (s, 2H), 3.03-3.01 (d, J=4.2 Hz, 3H), 2.42 (s, 3H)

Example 15. Preparation of 1-(2,3-dimethoxy-benzyl)-3-methyl-thiourea (JC1-15)

A white solid (65 mg, 0.27 mmol) was obtained in the same manner as in Example 3, but by using 2,3-dimethoxybenzylamine. (Yield: 45%)
¹H-NMR (300 MHz, CDCl₃) δ7.27-7.05 (m, 3H), 4.78 (s, 2H), 4.09-4.07 (d, J=5.9 Hz, 6H), 3.16-3.15 (d, J=5.5 Hz, 3H)

Example 16. Preparation of 1-(2-ethoxy-benzyl)-3-methyl-thiourea (JC1-16)

Yellow oil (128 mg, 0.57 mmol) was obtained in the same manner as in Example 3, but by using 2-ethoxybenzylamine. (Yield: 86%)
¹H-NMR (300 MHz, CD3OD) δ7.20-7.16 (m, 2H), 6.90-6.82 (m, 2H), 4.62 (s, 2H), 4.08-4.01 (q, J=13.9 Hz, 2H), 2.92 (s, 3H), 1.41-1.37 (t, J=7 Hz, 3H)

Example 17. Preparation of 1-(3-nitro-benzyl)-3-methyl-thiourea (JC1-(17)

A yellow solid (113 mg, 0.50 mmol) was obtained in the same as in Example 1, but by using 3-nitrobenzylamine. (Yield: 77%)
¹H-NMR (300 MHz, CD3OD) δ8.18 (s, 1H), 8.11-8.09 (d, J=7.7 Hz, 1H), 7.73-7.71 (d, J=7.5 Hz, 1H), 7.57-7.52 (t, J=7.9 Hz, 1H), 4.86 (s, 2H), 2.95 (s, 3H)

Example 18. Preparation of 1-(2-nitro-benzyl)-3-methyl-thiourea (JC1-18)

A yellow solid (64 mg, 0.28 mmol) was obtained in the same manner as in Example 1, but by using 2-nitrobenzylamine. (Yield: 43%)
¹H-NMR (300 MHz, CD3OD) δ8.01-7.99 (m, 1H), 7.63-7.54 (m, 2H), 7.46-7.40 (m, 1H), 4.97 (s, 2H), 2.90 (s, 3H)

Example 19. Preparation of 1-(3,4,5-trimethoxy-benzyl)-3-methyl-thiourea (JC1-19)

A white solid (126 mg, 0.47 mmol) was obtained in the same manner as in Example 3, but by using 3,4,5-trimethoxybenzylamine. (Yield: 92%)
$^1$H-NMR (300 MHz, DMSO) δ6.64 (d, J=2.2 Hz, 2H), 6.36-6.34 (t, J=2.2 Hz, 2H), 4.62 (s, 2H), 3.74 (s, 6H), 2.94 (s, 3H)

Example 20. Preparation of 1-(3,5-dimethoxy-benzyl)-3-methyl-thiourea (JC1-20)

A white solid (101 mg, 0.42 mmol) was obtained in the same manner as in Example 3, but by using 3,5-dimethoxybenzylamine. (Yield: 70%)
$^1$H-NMR (300 MHz, CD3OD) δ6.48-6.47 (d, 2H), 4.55 (s, 2H), 3.74 (s, 6H), 3.62 (s, 3H), 2.84 (s, 3H)

Example 21. Preparation of 1-(2,4-dichloro-benzyl)-3-methyl-thiourea (JC1-21)

A white solid (101 mg, 0.54 mmol) was obtained in the same manner as in Example 3, but by using 2,4-dichlorobenzylamine. (Yield: 94%)
$^1$H-NMR (300 MHz, CDCl$_3$): δ10.04 (s, 1H), 8.13 (d, 2H, J=8.40 Hz), 7.95 (m, 3H), 7.43 (d, 1H, J=3.30)

Example 22. Preparation of 1-(3,4-dihydroxy-benzyl)-3-methyl-thiourea JC1-22)

As in Reaction Scheme 1, TEA (0.04 ml, 0.27 mmol) was added to 3,4-dihydroxybenzylamine (50 mg, 0.23 mmol) in the presence of dimethylformamide solvent, and then N-methylisothiocyante (0.03 ml, 0.50 mmol) was added thereto, followed by stirring. After confirming by TLC that the base compound had disappeared, the solvent was removed and the solid was filtered off using methylene chloride and a vacuum filter to obtain a yellow solid (29 mg, 0.14 mmol). (Yield: 58%)
$^1$H-NMR (300 MHz, CD3OD) δ6.76-6.60 (m, 3H), 4.50 (s, 2H), 2.98 (s, 3H)

Example 23. Preparation of 1-(2,4-dimethoxy-benzyl)-3-methyl-thiourea (JC1-23)

A white solid (122.3 mg, 0.51 mmol) was obtained in the same manner as in Example 3, but by using 2,4-dimethoxybenzylamine. (Yield: 85%)
$^1$H-NMR (300 MHz, CD3OD) δ7.24-7.15 (m, 1H), 6.43-6.40 (m, 2H) 4.46 (s, 2H), 3.80-3.76 (d, J=12.1 Hz, 6H), 2.93 (s, 3H)

Example 24. Preparation of 1-(4-phenyl-benzyl)-3-methyl-thiourea (JC1-24)

A white solid (364 mg, 1.42 mmol) was obtained in the same manner as in Example 3, but by using 4-phenylbenzylamine. (Yield: 87%)
$^1$H-NMR (300 MHz, CDCl$_3$): δ8.61 (dd, 1H, J=1.37, 4.67 Hz), 7.96 (d, 2H, J=8.43 Hz), 7.83 (m, 4H), 7.57 (d, 2H, J=8.79 Hz), 7.38 (d, 2H, J=8.61 Hz), 7.26 (m, 1H), 1.31 (s, 9H)

Example 25. Preparation of 1-(3-hydroxy-4-methoxy-benzyl)-3-methyl-thiourea (JC1-25)

A white solid (472 mg, 2.09 mmol) was obtained in the same manner as in Example 1, but by using 3-hydroxy-4-methoxybenzylamine. (Yield: 64%)
$^1$H-NMR (300 MHz, CD3OD) δ6.82-6.68 (m, 3H), 4.50 (s, 2H), 3.77 (s, 3H), 2.89 (s, 3H)

Example 26. Preparation of 1-(4-cyano-benzyl)-3-methyl-thiourea (JC1-26)

A yellow solid (100 mg, 0.49 mmol) was obtained in the same manner as in Example 1, but by using 4-cyanobenzylamine. (Yield: 82%)
$^1$H-NMR (300 MHz, CDCl$_3$) δ7.79-7.76 (d, J=8.2 Hz, 2H), 7.45-7.43 (d, J=8.1 Hz 5H) 4.74 (s, 2H) 2.83 (s, 4H)

Example 27. Preparation of 1-(3,4-dichloro-benzyl)-3-methyl-thiourea (JC1-27)

A white solid (56 mg, 0.23 mmol) was obtained in the same manner as in Example 3, but by using 3,4-dichlorobenzylamine. (Yield: 39%)
$^1$H-NMR (300 MHz, CD3OD) δ7.47-7.42 (m, 2H), 7.79-7.76 (dd, J=8.3 Hz, 1H), 4.66 (s, 2H), 2.84 (s, 3H)

Example 28. Preparation of 1-(3-chloro-benzyl)-3-methyl-thiourea (JC1-28)

A white solid (156 mg, 0.70 mmol) was obtained in the same manner as in Example 3, but by using 3-chlorobenzylamine. (Yield: 90%)
$^1$H-NMR (400 MHz, DMSO) δ7.36-7.23 (m, 4H), 7 4.70 (s, 2H), 2.93 (s, 3H)

Example 29. Preparation of 1-(3-fluoro-benzyl)-3-methyl-thiourea (JC1-29)

A yellow solid (269 mg, 1.36 mmol) was obtained in the same manner as in Example 3, but by using 3-fluorobenzylamine. (Yield: 75%)
$^1$H-NMR (300 MHz, CD3OD) δ7.38-7.30 (m, 1H), 7.13-7.00 (m, 3H), 4.67 (s, 2H), 2.83 (s, 3H)

Example 30. Preparation of 1-(4-fluoro-benzyl)-3-methyl-thiourea (JC1-30)

A white solid (64 mg, 0.32 mmol) was obtained in the same manner as in Example 3, but by using 4-fluorobenzylamine. (Yield: 81%)
$^1$H-NMR (300 MHz, CD3OD) δ7.35-7.30 (m, 2H), 7.05-6.99 (m, 2H), 4.68 (s, 2H), 2.93 (s, 3H)

Example 31. Preparation of 1-(3,4-difluoro-benzyl)-3-methyl-thiourea (JC1-31)

A white solid (84 mg, 0.39 mmol) was obtained in the same manner as in Example 3, but by using 3,4-difluorobenzylamine. (Yield: 55%)
$^1$H-NMR (400 MHz, DMSO) δ7.40-7.13 (m, 3H), 4.63 (s, 2H), 2.83 (s, 3H)

Example 32. Preparation of 1-(2,4-difluoro-benzyl)-3-methyl-thiourea (JC1-32)

A yellow solid (199 mg, 0.92 mmol) was obtained in the same manner as in Example 3, but by using 2,4-difluorobenzylamine. (Yield: 99%)
$^1$H-NMR (400 MHz, CD3OD) δ7.42-7.37 (m, 1H), 6.93-6.88 (m, 2H), 4.72 (s, 2H), 2.94 (s, 3H)

Example 33. Preparation of 1-(2,3-dichloro-benzyl)-3-methyl-thiourea (JC1-33)

A white solid (107 mg, 0.43 mmol) was obtained in the same manner as in Example 3, but by using 2,3-dichlorobenzylamine. (Yield: 75%)

$^1$H-NMR (300 MHz, DMSO) δ7.54-7.51 (m, 1H), 7.36-7.31 (t, J=7.8 Hz, 1H), 7.24-7.21 (d, J=7.7 Hz, 1H), 4.72 (s, 2H), 2.84 (s, 3H)

Example 34. Preparation of 1-(2-chloro-benzyl)-3-methyl-thiourea (JC1-34)

A yellow solid (134 mg, 1.60 mmol) was obtained in the same manner as in Example 3, but by using 2-chlorobenzylamine. (Yield: 88%)

$^1$H-NMR (300 MHz, DMSO) δ7.38-7.20 (m, 4H), 4.79 (s, 2H), 2.96 (s, 3H)

Example 35. Preparation of R-(+)-1-[1-(4-methoxy-phenyl)-ethyl]-3-methyl-thiourea (JC1-35)

A yellow solid (181 mg, 0.80 mmol) was obtained in the same manner as in Example 3, but by using (R)-(+)-4-methoxy-a-methylbenzylamine. (Yield: 99%)

$^1$H-NMR (300 MHz, DMSO) δ7.17-7.14 (d, J=8.6 Hz, 2H), 6.88-6.85 (d, J=8.6 Hz, 1H), 5.33 (s, 1H), 3.71 (s, 3H), 2.83-2.81 (d, J=4.2 Hz, 3H), 1.38-1.36 (d, J=6.8 Hz, 3H)

Example 36. Preparation of S-(−)-1-[1-(4-methoxy-phenyl)-ethyl]-3-methyl-thiourea (JC1-36)

Yellow oil (170 mg, 0.76 mmol) was obtained in the same manner as in Example 3, but by using (S)-(−)-4-methoxy-a-methylbenzylamine. (Yield: 99%)

$^1$H-NMR (300 MHz, DMSO) δ7.17-7.14 (m, 2H), 6.79-6.74 (m, 2H), 5.21 (s, 1H), 3.66 (s, 3H), 2.82 (s, 3H), 1.37-1.34 (d, J=6.8 Hz, 3H)

Example 37. Preparation of N-4-[(3-methyl-thioureido)-methyl]-phenyl-methanesulfonamide (JC1-37)

TEA (1.2 eq) and 4-metylaminobenzylisothiocyanate (1 eq) were added to a methylamine hydrochloride salt (1 eq) in the presence of DMF solvent, followed by stirring. After confirming by TLC that the base compound had disappeared, DMF was removed. Thereafter, the resulting product was diluted with ethyl acetate, washed with brine, and then evaporated under reduced pressure to obtain a residue, and the residue was subjected to column chromatography (hexane:ethyl acetate=3:1). (Yield: 80%)

1H-NMR (300 MHz, CD3OD) δ7.31-7.28 (m, 2H), 7.22-7.18 (m, 2H), 4.67 (s, 2H), 2.98 (s, 3H), 2.85 (s, 3H)

Example 38. Preparation of 1-methyl-3-(4-pyridinyl-2-benzyl)-thiourea (JC1-38)

As in Reaction Scheme 2,4-(2-pyridyl)benzaldehyde (97%, 1,000 mg, 5.46 mmol) and N-methylthiourea (4,921 mg, 54.6 mmol) were put in a two-necked round-bottom flask, and then the pressure therein was reduced, followed by replacing the atmosphere in the flask with argon gas. Subsequently, anhydrous tetrahydrofuran (THF, 20 ml) solvent was added thereto, and freeze-stored Ti(OiPr)$_4$ (2.72 ml, 9.28 mmol) was added thereto, followed by reflux. When the base compound had completely disappeared as confirmed by TLC, the reaction vessel was slowly cooled, and then sodium borohydride (103 mg, 2.73 mmol) was added thereto. As a result, a desired yellow product (512.9 mg, 2 mmol) was obtained. (Yield: 37%)

$^1$H-NMR (300 MHz, CDCl$_3$) δ8.67-8.65 (d, J=5.0 Hz, 1H), 7.95-7.92 (d, J=8.2 Hz, 2H), 7.78-7.68 (m, 2H), 7.42-7.39 (d, J=8.0 Hz, 2H), 7.21 (s, 1H), 4.71 (s, 2H), 2.99 (s, 3H)

Example 39. Preparation of 1-(2-allyloxy-benzyl)-3-methyl-thiourea (JC1-39)

A white solid (330.2 mg, 1.40 mmol) was obtained in the same manner as in Example 37, but by using 2-allyloxy-benzaldehyde. (Yield: 45%)

$^1$H-NMR (300 MHz, CDCl$_3$) δ7.29-7.20 (m, 2H), 6.98-6.74 (m, 2H), 6.11-5.99 (m, 1H), 5.43-5.27 (m, 2H), 4.57 (s, 2H), 4.55 (s, 2H), 2.91 (s, 3H)

Example 40. Preparation of 1-(4-benzyloxy-benzyl)-3-methyl-thiourea (JC1-40)

A yellow solid (202.7 mg, 0.71 mmol) was obtained in the same manner as in Example 37, but by using 4-benzyloxy-benzaldehyde. (Yield: 30%).

$^1$H-NMR (300 MHz, CD3OD) δ7.44-7.28 (m, 5H), 7.23-7.20 (d, J=8.4 Hz, 2H), 6.98-6.94 (m, 2H), 5.07 (s, 2H), 4.55 (s, 2H), 2.82 (s, 3H)

Example 41. Preparation of 1-(3-benzyloxy-4-methoxy-benzyl)-3-methyl-thiourea (JC1-41)

A white solid (263.4 mg, 0.83 mmol) was obtained in the same manner as in Example 37, but by using 3-benzyloxy-4-methoxybenzaldehyde. (Yield: 39%)

$^1$H-NMR (300 MHz, DMSO) δ7.46-7.32 (m, 5H), 7.05 (s, 1H), 6.92-6.90 (d, J=8.3 Hz, 1H), 6.84-6.81 (d, J=8.2 Hz, 1H), 5.02 (s, 2H), 4.52 (s, 2H), 3.73 (s, 3H), 2.81 (s, 3H)

Example 42. Preparation of 1-(4-phenoxy-benzyl)-3-methyl-thiourea (JC1-42)

A yellow solid (178.9 mg, 0.66 mmol) was obtained in the same manner as in Example 37, but by using 4-phenoxy-benzaldehyde. (Yield: 65%)

$^1$H-NMR (300 MHz, CDCl$_3$) δ7.33-7.23 (m, 4H), 7.11-7.06 (m, 1H), 6.98-6.92 (m, 4H), 4.62 (s, 2H), 2.96-2.94 (d, J=4.6 Hz, 3H)

Example 43. Preparation of 1-methyl-3-naphthalene-2-methyl-thiourea (JC1-43)

N-methyl thiourea (163.1 mg, 1.8 mmol) was added to 2-bromomethyl naphthalene (200 mg, 0.90 mmol) in the presence of methanol solvent, followed by stirring. After confirming by TLC that the base compound had disappeared, methanol was vacuum distilled. The residue was dissolved again in a minimum amount of methanol, and then the solution was diluted with ethyl acetate and then washed with brine. At this time, a white solid was filtered off. The residue obtained after vacuum distillation was subjected to column chromatography (ethyl acetate:methanol=7:1) to obtain a white solid (118.0 mg, 0.51 mmol). (Yield: 57%)

$^1$H-NMR (400 MHz, DMSO) δ7.91-7.86 (m, 4H), 7.55-7.51 (m, 3H), 4.71 (s, 2H), 2.83 (s, 3H)

General Experimental Methods for Reaction Scheme 3

(Experimental Method 1)
2-Ethoxy-4-bromo-benzonitrile 4-fluoro-2-hydroxybenzonitrile (50 mg, 0.32 mmol) and DMF (2 ml) were put in a round-bottom flask and stirred, finely ground potassium carbonate (133 mg, 0.96 mmol) was added thereto, and then iodoethane (0.03 ml, 0.39 mmol) was added thereto, followed by stirring. After confirming by TLC that the base compound had disappeared, DMF was vacuum-distilled, and the residue was diluted with ethyl acetate and then washed with brine. The residue obtained after vacuum distillation was subjected to column chromatography (hexane:ethyl acetate=5:1) to obtain 2-ethoxy-4-bromo-benzonitrile (53.8 mg). (Yield: 94%)

(Experimental Method 2)
2-Ethoxy-4-aryl-benzonitrile

DMF (1 ml) was added to the 1-methyl-3-naphthalene-2-methyl-thiourea (50 mg, 0.22 mmol) obtained according to Experimental Method 1, aryl boronic acid (32.4 mg, 0.27 mmol), palladium (II) acetate (0.5 mg, 0.0002 mmol), p-acetoacetanisidide (1.3 mg, 0.007 mmol), and cesium carbonate (61.1 mg, 0.44 mmol), followed by warming to 80° C. and stirring. The color of the reaction solution was observed to turn brown. After confirming by TLC that the base compound had disappeared, DMF was vacuum-distilled. The material deposited as a solid was filtered off, the filtrate was vacuum-distilled, the residue obtained after vacuum distillation was subjected to column chromatography to isolate 2-ethoxy-4-aryl-benzonitrile.

(Experimental Method 3)
2-Ethoxy-4-aryl-benzylamine

A reflux device and a two-necked round bottom flask were dried in an oven, and then cooled, installed, and then the pressure therein was reduced. Thereafter, in a state in which the atmosphere in the flask was replaced with argon gas, lithium aluminum hydride (212.9 mg, 5.61 mmol) and anhydrous diisopropyl ether (20 ml) were added thereto, and then refluxed. Thereafter, the 2-ethoxy-4-aryl-benzonitrile (1.87 mmol) obtained according to Experimental Method 2 was dissolved in a solvent, and the solution was transferred to the flask through a cannula, and then stirred. After confirming by TLC that the base compound had disappeared, 1N-HCl was added to the flask until the solution became neutral, followed by stirring. Subsequently, an appropriate amount of Rochelle salt was added to the flask and the resulting solution was stirred for about 30 minutes. After Celite was put in a vacuum filter, the reaction solution was poured into Celite for filtration. The filtrate was acidified with 1N-HCl and extracted as a water layer, and the extract was basified using sodium bicarbonate and extracted as ethyl acetate. This process was repeated several times to obtain desired 2-ethoxy-4-aryl-benzylamine.

(Experimental Method 4) 1-(2-Ethoxy-4-aryl-benzyl)-3-methyl-thiourea 1-(2-Ethoxy-4-aryl-benzyl)-3-methyl-thiourea was obtained in the same manner as in Example 1, but by using the 2-ethoxy-4-aryl-benzylamine obtained using Experimental Method 3.

Example 44. Preparation of 1-(3-ethoxy-biphenyl-4-methyl)-3-methyl-thiourea (JC1-44)

A desired yellow solid (348.2 mg, 1.16 mmol) was obtained by conducting an experiment according to Experimental Methods 1, 2, 3, and 4, using phenyl boronic acid for Experimental Method 2. (Total yield: 79%)
$^1$H-NMR (400 MHz, CD$_3$OD) δ7.40-7.37 (d, 2H), 7.43-7.38 (m, 2H), 7.33-7.26 (m, 2H), 7.14-7.12 (m, 2H), 4.33 (s, 2H), 4.19-4.12 (q, J=13.9 Hz, 2H), 2.71 (s, 3H), 1.48-1.43 (t, J=7.0 Hz, 3H)

Example 45. Preparation of (4'-tert-butyl-3-ethoxy-biphenyl-4-methyl)-thiourea (JC1-45)

A desired yellow liquid (55.6 mg, 0.16 mmol) was obtained by conducting an experiment according to Experimental Methods 1, 2, 3, and 4, using 4-tert-butylphenyl boronic acid for Experimental Method 2. (Total yield: 32%)
$^1$H-NMR (300 MHz, CDCl$_3$) δ7.49-7.42 (m, 4H), 7.33-7.30 (d, J=7.7 Hz, 1H), 7.13-7.10 (m, 1H), 7.04 (s, 1H), 4.61 (s, 2H), 4.17-4.10 (q, J=13.9 Hz, 2H), 2.97-2.96 (d, J=3.8 Hz, 3H), 1.48-1.43 (t, J=7.0 Hz, 3H), 1.34 (s, 9H)

Example 46. Preparation of 1-(3,3'-diethoxy-biphenyl-4-methyl)-3-methyl-thiourea (JC1-46)

A desired compound (444 mg, 1.29 mmol) was obtained by conducting an experiment according to Experimental Methods 1, 2, 3, and 4, using 4-ethoxyphenyl boronic acid for Experimental Method 2. (Total yield: 45%)
$^1$H-NMR (300 MHz, CDCl$_3$) δ7.50-7.48 (m, 2H), 7.37-7.32 (m, 2H) 7.27-7.23 (m, 3H), 7.09-7.05 (m, 3H), 4.57 (s, 2H), 4.19-4.12 (t, J=13.9 Hz, 3H), 2.99-2.80 (d, J=4.41 Hz, 3H), 1.59 (s, 3H), 1.50-1.45 (t, J=7 Hz, 3H)

Example 47. Preparation of 1-(2-ethoxy-4-styryl-benzyl)-3-methyl-thiourea (JC1-47)

A desired yellow solid (30 mg, 0.09 mmol) was obtained by conducting an experiment according to Experimental Methods 1, 2, 3, and 4, using 4-styryl boronic acid for Experimental Method 2. (Total yield: 8%)
$^1$H-NMR (300 MHz, CDCl$_3$) δ7.50-7.48 (m, 2H), 7.37-7.32 (m, 2H) 7.27-7.23 (m, 3H), 7.09-7.05 (m, 3H), 4.57 (s, 2H), 4.19-4.12 (t, J=13.9 Hz, 3H), 2.99-2.80 (d, J=4.4 Hz, 3H), 1.59 (s, 3H), 1.50-1.45 (t, J=7 Hz, 3H)

Example 48. Preparation of 1-(3-ethoxy-4'-trifluoromethyl-biphenyl-4-methyl)-3-methyl-thiourea (JC1-48)

A desired compound (93 mg, 0.25 mmol) was obtained by conducting an experiment according to Experimental Methods 1, 2, 3, and 4, using 4-trifluorophenyl boronic acid for Experimental Method 2. (Total yield: 24%)
$^1$H-NMR (300 MHz, CDCl$_3$) δ7.62-7.54 (dd, J=13.4 Hz, 4H), 7.34-7.31 (d, J=13.4 Hz, 1H), 7.08-7.05 (m, 1H), 6.98 (s, 1H), 4.59 (s, 2H), 4.14-4.05 (q, J=13.9 Hz, 2H), 2.93-2.91 (d, J=4.2 Hz, 3H), 1.44-1.40 (t, J=7 Hz, 3H)

Example 49. Preparation of 1-methyl-3-(3-phenoxy-benzyl)-thiourea (JC1-50)

A desired compound (572.7 mg, 2.1 mmol) was obtained in the same manner as in Example 37, but by using 3-phenoxy benzaldehyde (97%, 500 mg, 2.52 mmol). (Yield: 84%)

$^1$H-NMR (400 MHz, CD3OD) δ7.33-7.25 (m, 2H), 7.09-7.05 (m, 2H), 6.96-6.95 (m, 3H), 6.84-6.82 (dd, J=4.8 Hz, 1H), 4.68 (s, 2H), 2.92 (s, 3H)

Example 50. Preparation of 1-methyl-3-(2-phenoxy-benzyl)-thiourea (JC1-51)

A desired compound (255.7 mg, 0.94 mmol) was obtained in the same manner as in Example 37, but by using 2-phenoxy benzaldehyde (900 mg, 3.94 mmol). (Yield: 24%)
$^1$H-NMR (300 MHz, CD3OD) δ7.40-7.31 (m, 3H), 7.26-7.21 (m, 1H), 7.13-7.06 (m, 2H), 6.98-6.95 (m, 2H), 6.85-6.82 (m, 1H), 4.72 (s, 2H), 2.90 (s, 3H)

(Additional Experimental Method) 2-Phenoxy benzaldehyde

As in Reaction Scheme 4, commercially available 2-fluorobenzaldehyde (200 mg, 1.61 mmol) was used as a starting material. Phenol (152 mg, 1.61 mmol) was nucleophilically added using potassium carbonate (245 mg, 1.77 mmol) base in the presence of DMF (3 ml) solvent, thereby synthesizing 2-phenoxy benzaldehyde (183 mg, 0.92 mmol). (Yield: 57%)

Example 51. Preparation of 1-[4-(4-fluoro-phenoxy)-benzyl]-3-methyl-thiourea (JC1-52)

A desired compound (447 mg, 1.56 mmol) was obtained in the same manner as in Example 37, but by using 4-(4-fluorophenoxy)benzaldehyde (500 mg, 2.31 mmol). (Yield: 67%)
$^1$H-NMR (300 MHz, CDCl$_3$) δ7.28-7.26 (m, 2H), 7.05-6.91 (m, 6H), 4.64-4.62 (d, J=4.7 Hz, 2H), 2.98-2.97 (d, J=5.0 Hz, 3H)

Example 52. Preparation of 1-[4-(4-methoxy-phenoxy)-benzyl]-3-methyl-thiourea (JC1-53)

A desired compound (553.2 mg, 1.56 mmol) was obtained in the same manner as in Example 37, but by using 4-(4-methoxyphenoxy)benzaldehyde (500 mg, 2.19 mmol). (Yield: 84%)
$^1$H-NMR (400 MHz, CDCl$_3$) δ7.24-7.20 (m, 2H), 6.93-6.84 (m, 6H), 4.58 (s, 2H), 2.93 (s, 3H)

[Experimental Examples]. Biological Efficacy Test

Experimental Example 1. Effect of Thiourea-Based Compound, e.g., JC1 Compound, on Transcriptional Activity of RORα

Figure 3:
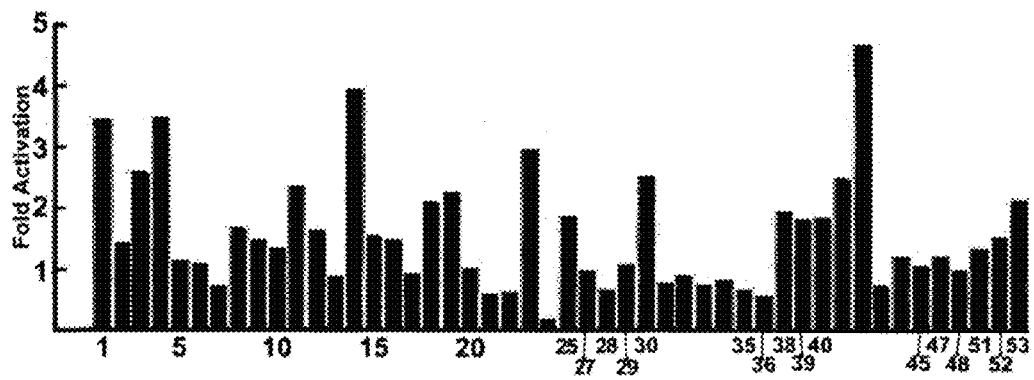
FIG. 3 illustrates the effects of JC1 compounds on the transcriptional activity of RORα.

CV-1 cells (CCL-70) were purchased from American Type Culture Collection (ATCC). The CV-1 cells (4×10$^4$ cells/well) were seeded on a 24-well culture plate and cultured overnight in a Dulbecco's Modified Eagle's Medium (DMEM) containing 10% fetal bovine serum (FBS). The CV-1 cells were maintained at 37° C. in a humidification thermostat containing 5% CO$_2$ and 95% air. After culturing, the cells were transformed with RORE-tk-Luc reporter plasmid (100 ng) and ROR expression vector (5 ng) using calcium phosphate.
HepG2 cells (1×10$^5$ cells/well) were seeded on a 12-well plate and cultured overnight. The cells were transformed with LXRE-Luc (100 ng) or SRE-Luc (100 ng) reporter plasmid using Welfect-EXTM Plus (WelGENE Inc., Korea). 24 hours after transformation, the cells were treated with JC1 compounds (100 μM), a solvent (control), and the like. 24 hours after treatment, luciferase activity was measured using an analytical luminescence luminometer. To determine transformation efficiency, luciferase activities were standardized using the activity of 200 ng of β-galactosidase (β-gal) expression vector. The results thereof are shown in Table 1, and the results of Table 1 are illustrated in FIG. 3.

TABLE 1

| Compound | Fold Activation |
|---|---|
| 1 | 3.4 |
| 2 | 1.4 |
| 3 | 2.6 |
| 4 | 3.4 |
| 5 | 1.1 |
| 6 | 1.1 |
| 7 | 0.7 |
| 8 | 1.7 |
| 9 | 1.4 |
| 10 | 1.3 |
| 11 | 2.3 |
| 12 | 1.6 |
| 13 | 0.9 |
| 14 | 3.9 |
| 15 | 1.5 |
| 16 | 1.4 |
| 17 | 0.9 |
| 18 | 2.1 |
| 19 | 2.2 |
| 20 | 1.0 |
| 21 | 0.6 |
| 22 | 0.6 |
| 23 | 2.9 |
| 24 | 0.2 |
| 25 | 1.9 |
| 26 | ND |
| 27 | 1.0 |
| 28 | 0.7 |
| 29 | 1.1 |
| 30 | 2.5 |
| 31 | 0.8 |
| 32 | 0.9 |
| 33 | 0.7 |
| 34 | 0.8 |
| 35 | 0.7 |
| 36 | 0.6 |
| 37 | ND |
| 38 | 1.9 |
| 39 | 1.8 |
| 40 | 3.6 |
| 41 | 2.5 |
| 42 | 4.6 |
| 43 | 0.7 |
| 44 | 1.2 |
| 45 | 1.0 |
| 46 | ND |
| 47 | 1.2 |
| 48 | 1.0 |
| 49 | ND |
| 50 | ND |
| 51 | 1.3 |
| 52 | 1.5 |
| 53 | 2.1 |

ND; not determined

As shown in Table 1 and FIG. 3, the JC1 compound increased the transcriptional activity of RORα. In particular, it was observed that 13 JC1 compounds exhibited activity that was twice or more that of the control, which had been treated only with a solvent, and, among these JC1 compounds, JC1-42 was observed to exhibit excellent activity as high as 460%.

Experimental Example 2. Effects of JC1-38, JC1-40, and JC1-42 on Transcriptional Activity of RORα According to Concentration CV-1 cells ($4 \times 10^4$ cells/well) were seeded on a 24-well culture plate and cultured overnight in a DMEM containing 10% FBS. The CV-1 cells were maintained at 37° C. in a humidification thermostat containing 5% $CO_2$ and 95% air. After culturing, the CV-1 cells were transformed with RORE-Luc reporter (0.05 μg) and Flag-RORα vector (0.005 μg) using calcium phosphate. 24 hours after transformation, the CV-1 cells were treated with particular concentrations (1 μM, 10 μM, 20 μM, 50 μM, and 100 μM) of JC1 compounds, in particular, highly chemically stable JC1-38, JC1-40, and JC1-42 among the 14 JC1 compounds observed in Experimental Example 1, and 100 μM melatonin, which is a ligand of RORα for 24 hours. Subsequently, cell lysates were collected, and luciferase activity was analyzed and determined using an analytical luminescence luminometer. The luciferase activity was standardized by β-gal activity to determine transcriptional efficiency, and data was attained as the mean and SD for two or three independent experimental results, and the results thereof are illustrated in FIG. 4.

Figure 4:
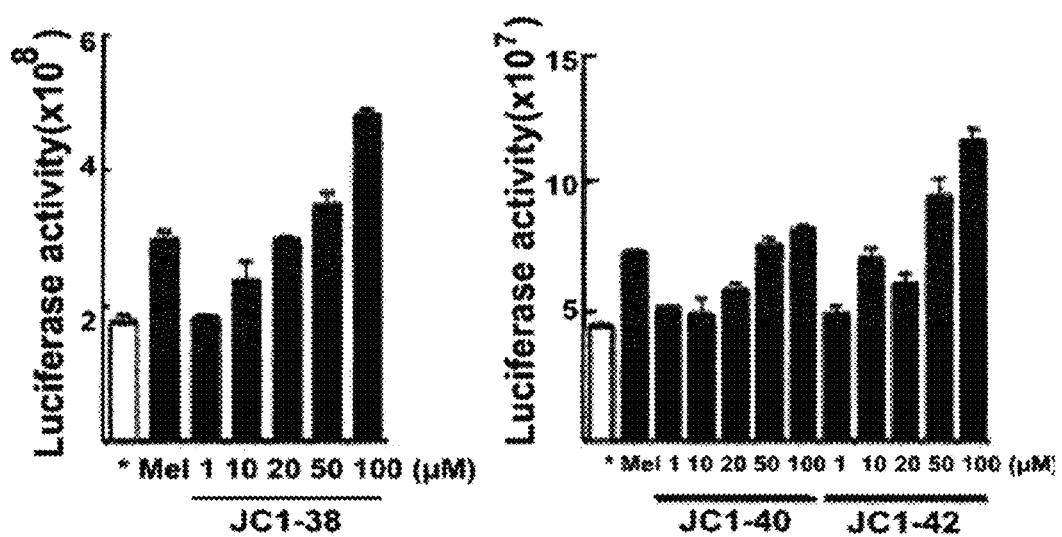
FIG. 4 illustrates changes in the transcriptional activity of RORα according to the concentration of JC1-38, JC1-40, and JC1-42.

As shown in FIG. 4, the transcriptional activity of RORα increased in a manner dependent on the concentration of JC1-38, JC1-40, and JC1-42. The activity of RORα was insignificantly increased by low concentrations (1 μM, 10 μM, and 20 μM) of JC1 compounds (JC1-38, JC1-40, and JC1-42), whereas, when the cells were treated with the JC1 compounds at a concentration of 50 μM to 100 μM, it was observed that the effect of increasing the activity of RORα provided by the JC1 compounds was comparable to or surpassed the effect provided by melatonin.

Experimental Example 3. Effects of JC1-38, JC1-40, and JC1-42 on Transcriptional Activities of LXRα and SREBP-1

A human hepatoma cell line and HepG2 (ATCC HB 8065) were purchased from ATCC. HepG2 cells ($1.2 \times 10^5$ cells/well) were seeded on a 24-well culture plate and cultured overnight in a DMEM containing 10% FBS. The HepG2 cells were maintained at 37° C. in a humidification thermostat containing 5% $CO_2$ and 95% air. After culturing, the HepG2 cells were transformed with LXRE-Luc reporter (0.1 μg) using Welfect-EXTM Plus (WelGENE Inc., Korea). 24 hours after transformation, the HepG2 cells were treated with particular concentrations (1 μM, 10 μM, 20 μM, 50 μM, and 100 μM) of JC1-38, JC1-40, and JC1-42 and 1 μM T17 (T0901317), which is a ligand of LXRα, for 24 hours. Subsequently, cell lysates were collected, and luciferase activity was analyzed and determined using an analytical luminescence luminometer. The luciferase activity was standardized by β-gal activity to determine transcriptional activity, and data was attained as the mean and SD for two or three independent experimental results, and the results thereof are illustrated in FIG. 5a.

Figure 5A:
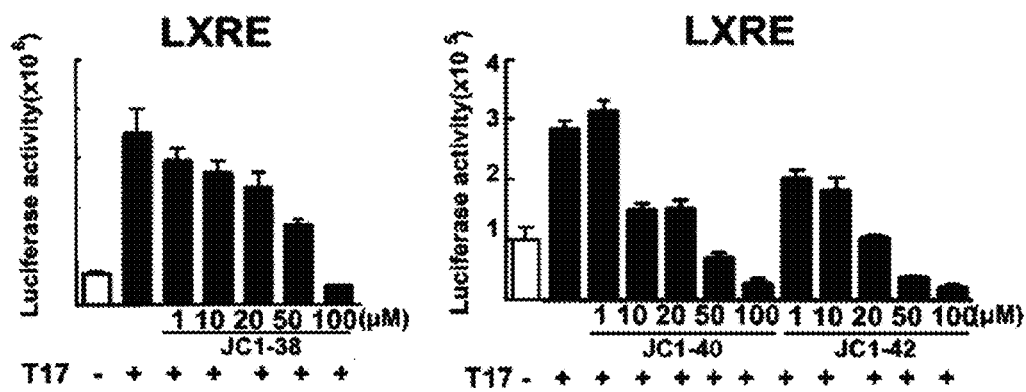
FIG. 5 illustrates the effects of JC1-38, JC1-40, and JC1-42 on the transcriptional activities of LXRα and SREBP-1.

As illustrated in FIG. 5a, the transcriptional activity of LXRα, which had been increased by T17, decreased in a manner dependent on the concentration of JC1-38, JC1-40, and JC1-42. In particular, it was observed that all three compounds at a concentration of 100 μM decreased the activity of LXRα, which had been induced by T17, by 90% or more.

In addition, HepG2 cells were cultured under the same conditions, and then the HepG2 cells were transformed with SRE-Luc reporter (0.1 μg) using Welfect-EXTM Plus (WelGENE Inc., Korea). 24 hours after transformation, the HepG2 cells were treated with each of the JC1-38, JC1-40, and JC1-42 compounds at a concentration of 50 μM and 1 μM T17 (T0901317) for 24 hours. Subsequently, cell lysates were collected, and luciferase activity was analyzed and determined using an analytical luminescence luminometer. The luciferase activity was standardized by β-gal activity to determine transcriptional efficiency, and data was attained as the mean and SD for three independent experimental results, and the results thereof are illustrated in FIG. 5b.

Figure 5B:
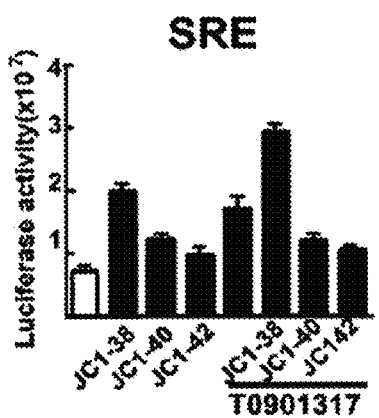

As illustrated in FIG. 5b, it was clearly seen that JC1-38, JC1-40, and JC1-42 decreased the transcriptional activity of SREBP-1, which had been increased by T17.

Experimental Example 4. Effects of JC1-38, JC1-40, and JC1-42 on Expression of LXRα, SREBP-1, and FAS Proteins HepG2 cells ($1 \times 10^6$ cells/well) were seeded on a 60-dish and cultured overnight in a DMEM containing 10% FBS. The HepG2 cells were maintained at 37° C. in a humidification thermostat containing 5% $CO_2$ and 95% air. After culturing, the HepG2 cells were treated with each of the JC1-38, JC1-40, and JC1-42 compounds at a concentration of 100 μM, and, as a positive control, the HepG2 cells were treated with 2 mM metformin, which is an AMPK activator, for 24 hours. After treatment, the expression of proteins was analyzed by western blotting analysis. That is, after treatment, the HepG2 cells were destroyed on ice in a lysis buffer containing 50 mM NaCl, 50 mM Tris pH 7.4, 5 mM EDTA, 1% NP-40, and a protease inhibitor for 30 minutes, and then centrifuged to obtain a total cell lysate. 20 μg to 30 μg of proteins collected from the total cell lysate was subjected to 7% to 9% sodium dodecyl sulfate-polyacrylamide gel electrophoresis (SDS-PAGE), and was transferred to a polyvinylidene difluoride membrane (Millipore, Bedford, Mass., USA). The resulting product was subjected to blocking with 5% or 10% (w/v) nonfat dry milk in PBS containing 0.1% Tween-20, and was reacted with antibodies specific to RORα (Affinity BioReagents), LXRα, SREBP-1, FAS (Santa Cruz Biotechnology), phospho-ACC (Cell signaling), and α-tubulin (Calbiochem). Immunoreactive proteins were detected with Amersham ECL western blotting detection reagents using a horseradish peroxidase (HRP)-conjugated secondary antibody (Zymed Lab). Protein concentrations were quantified by bicinchoninic acid (BCA) (Pierce) analysis, and the expression of α-tubulin was monitored as a control. The results thereof are illustrated in FIG. 6a.

Figure 6A:
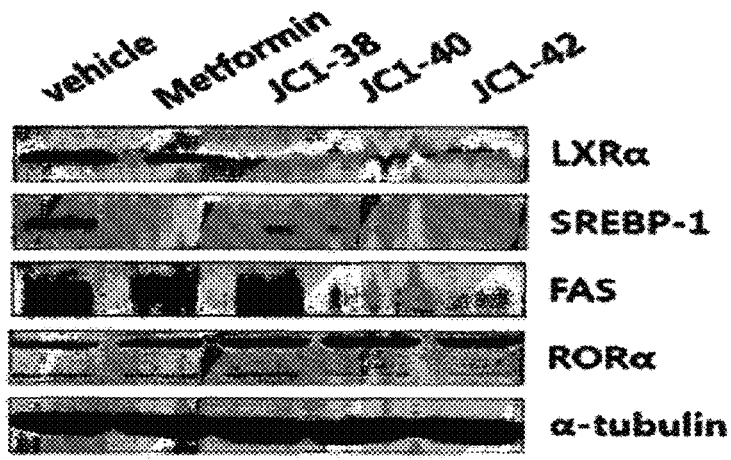
FIG. 6 illustrates the effects of JC1-38, JC1-40, and JC1-42 on the expression of LXRα, SREBP-1, and FAS proteins.

As illustrated in FIG. 6a, it was observed that the expression of LXRα, SREBP-1, and FAS proteins was decreased by JC1-40 and JC1-42, and the expression of LXRα and SREBP-1 proteins was decreased by JC1-38.

In addition, HepG2 cells were cultured under the same conditions, and then the HepG2 cells were treated with particular concentrations (0 μM, 1 μM, 10 μM, 50 μM, and 100 μM) of JC1-40 (or JC1-42) and 1 μM T17 for 24 hours. After treatment, the expression of proteins was analyzed by western blotting analysis, and the expression of α-tubulin was monitored as a control. The results thereof are illustrated in FIGS. 6b and 6c.

Figure 6B:
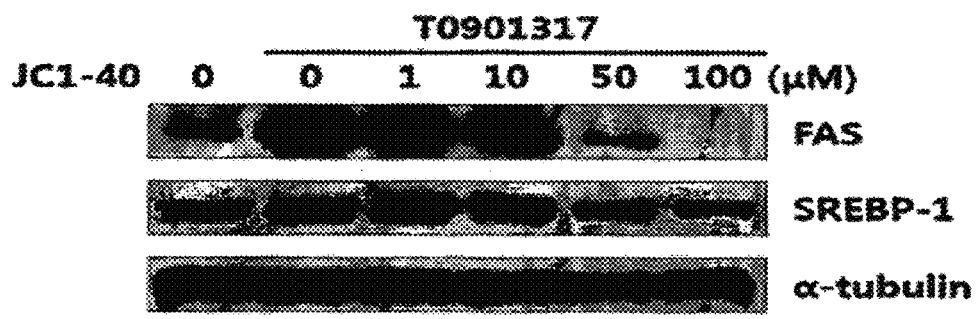
Figure 6C:
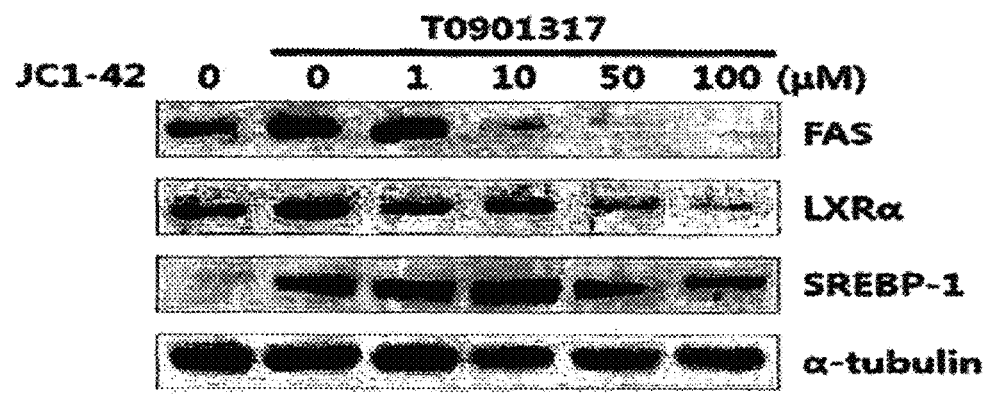

As illustrated in FIG. 6b, the expression of SREBP-1 and FAS, which had been increased by T17, decreased in a manner dependent on the concentration of JC1-40. In addition, as illustrated in FIG. 6c, the expression of LXRα, SREBP-1, and FAS, which had been increased by T17, decreased in a manner dependent on the concentration of JC1-42. In particular, it was observed that JC1-40 and JC1-42 at a concentration ranging from 50 μM to 100 μM strongly inhibited the expression of proteins (see FIGS. 6b and 6c).

Experimental Example 5. Effects of JC1-38, JC1-40, and JC1-42 on Phosphorylation of ACC HepG2 cells (1×10⁶ cells/well) were seeded on a 60-dish, and cultured overnight in a DMEM containing 10% FBS. The HepG2 cells were maintained at 37° C. in a humidification thermostat containing 5% CO2 and 95% air. After culturing, the HepG2 cells were treated with 100 μM JC1-38 and JC1-40 (or 100 μM JC1-38 and JC1-42), 2 mM metfornin, and 2 mM AICIR for 24 hours. After treatment, the expression of RORα and phosphorylated ACC (pACC) proteins was analyzed by western blotting, and the expression of α-tubulin was monitored as a control. The results thereof are illustrated in FIGS. 7a and 7b.

Figure 7A:
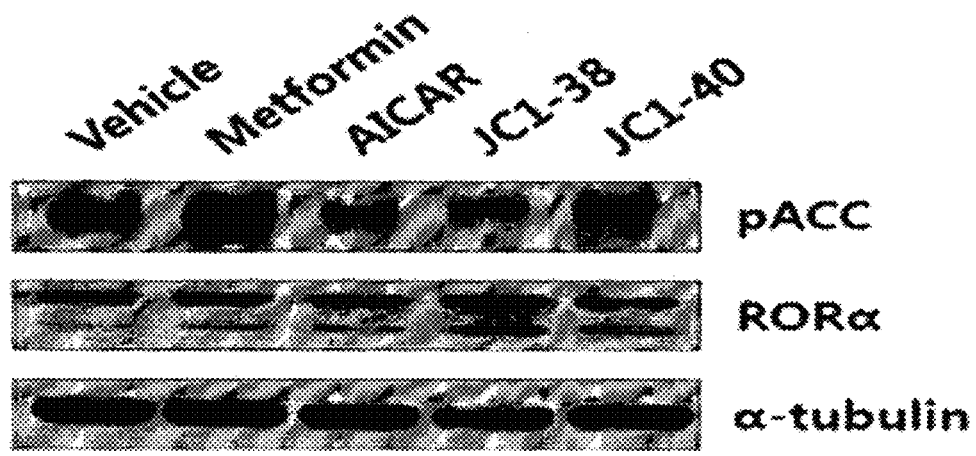
FIG. 7 illustrates the effects of JC1-40 and JC1-42 on the phosphorylation of ACC.
Figure 7B:
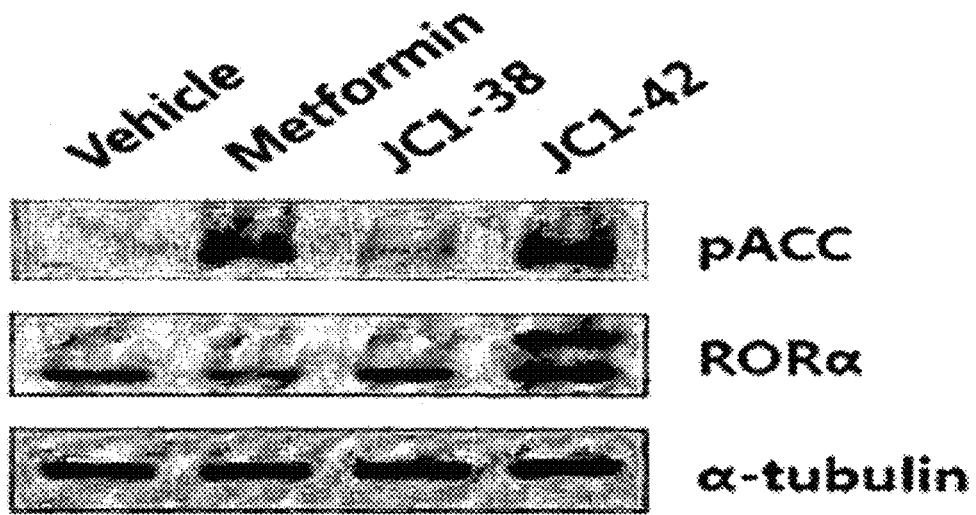

As illustrated in FIGS. 7a and 7b, the phosphorylation of ACC was increased by JC1-40 and JC1-42.

Experimental Example 6. Effects of JC1-38, JC1-40, and JC1-42 on Fatty Acid Oxidation in Hepatocytes HepG2 cells (1×10⁶ cells/well) were seeded on a 60-dish and cultured overnight in a DMEM containing 10% FBS. The HepG2 cells were maintained at 37° C. in a humidification thermostat containing 5% $CO_2$ and 95% air. After culturing, the HepG2 cells were treated with JC1-38, JC1-40, and JC1-42 at a concentration of 100 μM for 24 hours. After treatment, effects thereof on transcriptional activity were analyzed by real-time reverse transcriptase-polymerase chain reaction (real-time RT-PCR) analysis. The PCR was performed using the following primers respectively specific to MCAD, ACO1, ACO2, HMGCS2, CPT-1, and ACS, which are involved in fatty acid oxidation:

MCAD
(forward: 5'-CTACCAAGTATGCCCTGGAAAG-3' SEQ ID NO: 1, reverse: 5'-TGTGTTCACGGGCTACAATAAG-3' SEQ ID NO: 2), ACO1
(forward: 5'-GGGCATGGCTATTCTCATTGC-3' SEQ ID NO: 3, reverse: 5'-CGAACAAGGTCAACAGAAGTTAGGTTC-3' SEQ ID NO: 4), ACO2
(forward: 5'-GCGGACATGGCTACTCAAAGC-3' SEQ ID NO: 5, reverse: 5'-GCAGTGCACCTTAGCAGCCTG-3' SEQ ID NO: 6), HMGCS2
(forward: 5'-GGAACCCATATGGAGAATGTGT-3' SEQ ID NO: 7, reverse: 5'-TCCTGAGAGGCCTTTAGAAGTG-3' SEQ ID NO: 8), CPT1
(forward: 5'-AGACGGTGGAACAGAGGCTGAAG-3' SEQ ID NO: 9, reverse: 5'-TGAGACCAAACAAAGTGATGATGTCAG-3' SEQ ID NO: 10), ACS
(forward: 5'-AGCAGAGCTTCGCAGCGGC-3' SEQ ID NO: 11, reverse: 5'-TCTGCTGTTTTCGCTGGGTCC-3' SEQ ID NO: 12),
and β-actin
(5'-CGTGGGCCGCCCTAGGCACCA-3' SEQ ID NO: 13, reverse: 5'-TTGGCTTAGGGTTCAGGGGGG-3' SEQ ID NO: 14).

Figure 8:
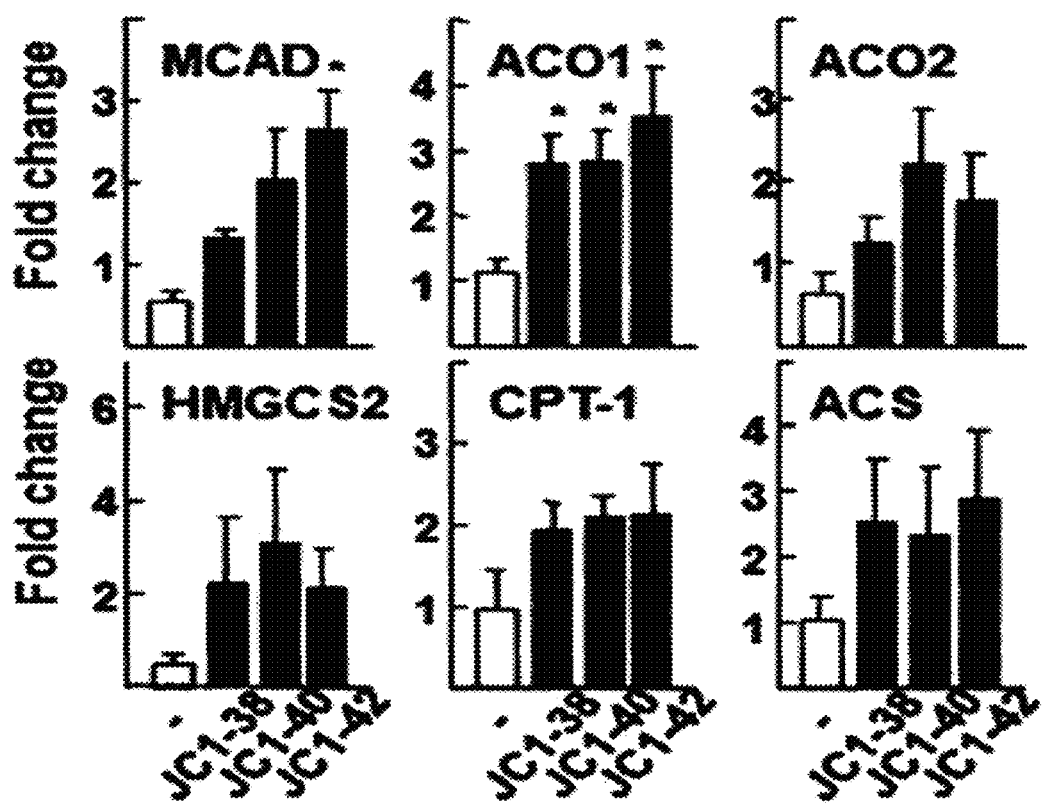
FIG. 8 illustrates the effects of JC1-38, JC1-40, and JC1-42 on fatty acid oxidation.

As illustrated in FIG. 8, it was observed that the transcriptional activities of MCAD, ACO1, ACO2, HMGCS2, CPT-1, and ACS, which are involved in fatty acid oxidation, were increased in HepG2 cells by JC1-38, JC1-40, and JC1-42.

Experimental Example 7. Effects of JC1-38, JC1-40, and JC1-42 on Fatty Acid Uptake and Secretion of Very Low Density Lipoproteins in Hepatocytes HepG2 cells (1×10⁶ cells/well) were seeded on a 60-dish, and cultured overnight in a DMEM containing 10% FBS. The HepG2 cells were maintained at 37° C. in a humidification thermostat containing 5% $CO_2$ and 95% air. After culturing, the HepG2 cells were treated with JC1-38, JC1-40, and JC1-42 at a concentration of 100 μM for 24 hours. After treatment, effects thereof on transcriptional activity were analyzed by RT-PCR analysis. The PCR was performed using the following primers respectively specific to CD36 (see FIG. 9a) involved in fatty acid uptake and MTTP and ApoB100 (see FIG. 9b), which are involved in the secretion of very low density lipoproteins:

CD36
(forward: 5'-GGAACTGTGGGCTCATTGC-3' SEQ ID NO: 15, reverse: 5'-CATGAGAATGCCTCCAAACAC-3' SEQ ID NO: 16), MTTP
(forward: 5'-CCTTCATTCAGCACCTCA-3' SEQ ID NO: 17, reverse: 5'-TGACAAGTGTCCCAGTGA-3' SEQ ID NO: 18), ApoB100
(forward: 5'-TAAATGGAGCACTTTTCAAG-3' SEQ ID NO: 19, reverse: 5'-GGAACAGCAGCAGTAGCG-3' SEQ ID NO: 20),
and β-actin
(5'-CGTGGGCCGCCCTAGGCACCA-3' SEQ ID NO: 13, reverse: 5'-TTGGCTTAGGGTTCAGGGGGG-3' SEQ ID NO: 14).

Figure 9A:
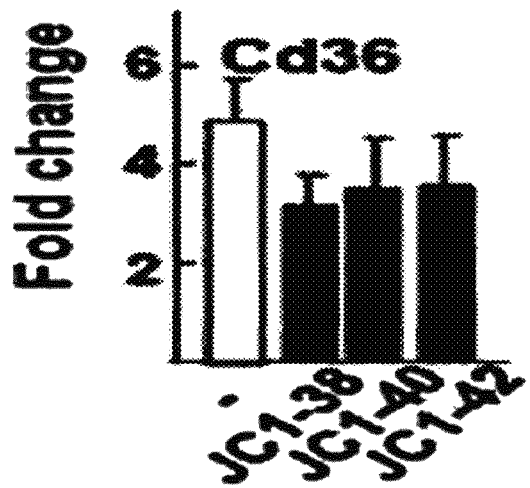
FIG. 9 illustrates the effects of JC1-38, JC1-40, and JC1-42 on fatty acid uptake and the secretion of very-low-density lipoproteins in hepatocytes.
Figure 9B:
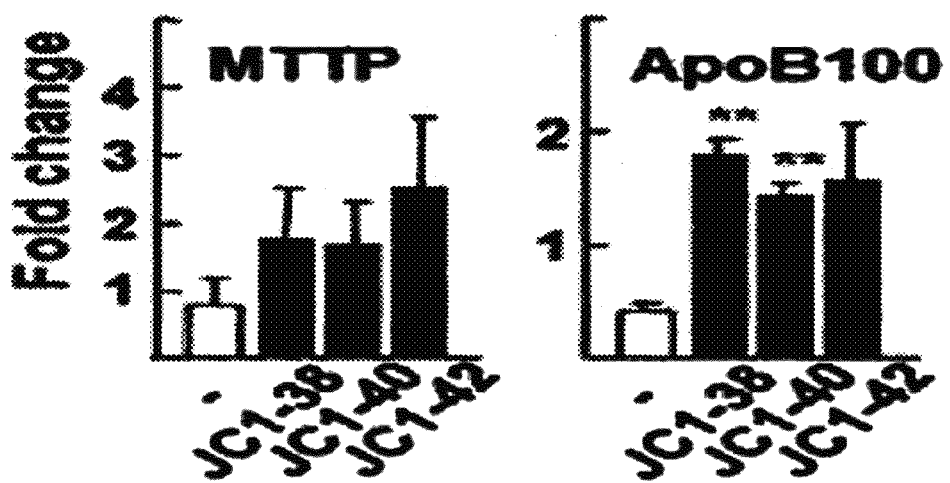

As illustrated in FIGS. 9a and 9b, it was observed in the HepG2 cells that, by JC1-38, JC1-40, and JC1-42, the transcriptional activity of CD36, which is involved in fatty acid uptake, was decreased and the transcriptional activities of MTTP and ApoB100, which are involved in the secretion of very low density lipoproteins, were increased.

Experimental Example 8. Effects of JC1-40 and JC1-42 on Lipid Accumulation in Hepatocytes HepG2 cells ($3\times10^5$ cells/well) were seeded on a 60-dish and cultured overnight in a DMEM containing 10% FBS. The HepG2 cells were maintained at 37° C. in a humidification thermostat containing 5% $CO_2$ and 95% air. After culturing, the HepG2 cells were treated with 50 μM JC1-40 (or JC1-42) and, as a lipid generation inducing material, a fatty acid mixture prepared by mixing 0.5 mM oleic acid and 0.5 mM palmitic acid in a ratio of 2:1 (5 mM oleic acid and 5 mM palmitic acid were mixed in a medium containing 1% fatty acid-free bovine serum albumin (BSA) and diluted to the final concentration prior to use) for 3 days. After 3 days, cell lysates were collected, and stained with 1 μg/ml of Nile red at room temperature for 15 minutes, and the concentration of triglycerides was measured by a flow cytometry method using a FACSCalibur™ machine (BD Biosciences). Fluorescence emission was measured at a wavelength between 500 nm and 580 nm. The results thereof are illustrated in FIGS. 10a and 10b.

Figure 10A:
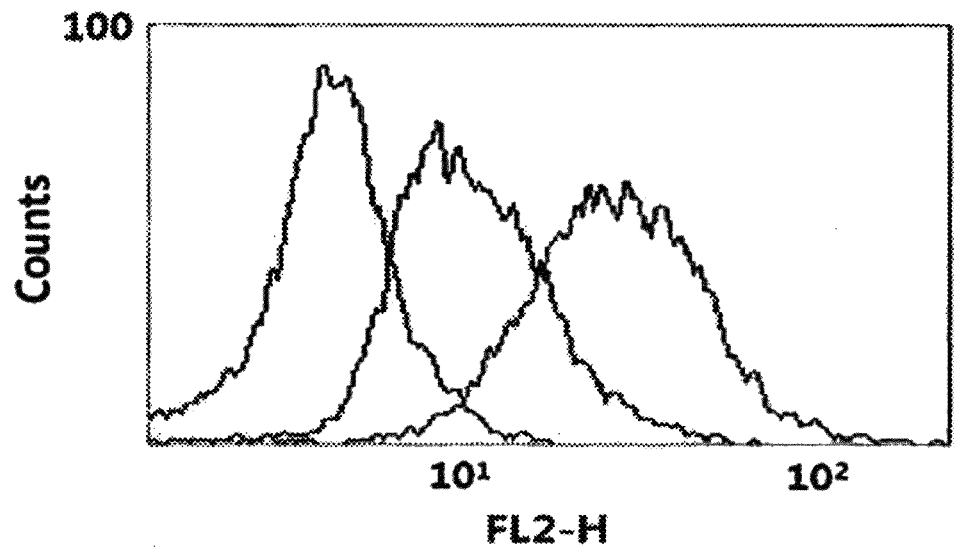
FIG. 10 illustrates the effects of JC1-40 and JC1-42 on the lipid accumulation of hepatocytes.
Figure 10B:
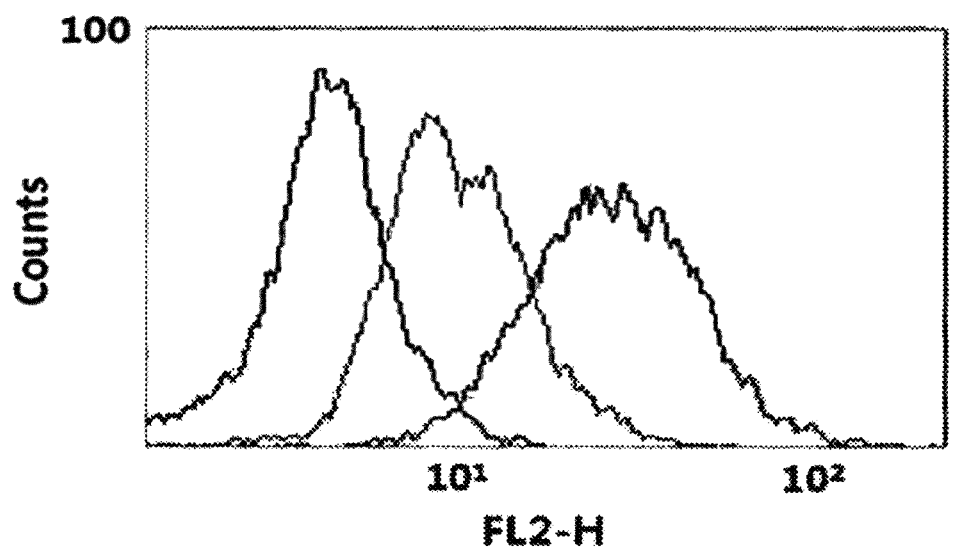

As illustrated in FIGS. 10a and 10b, the line on the leftmost side denotes a control treated only with a solvent, the middle line denotes an experimental group treated with JC1-40 or JC1-42 and fatty acid, and the line on the rightmost side denotes a control treated only with fatty acid, and it was observed that lipid accumulation in hepatocytes was significantly decreased by treatment with JC1-40 or JC1-42.

Figure 11A:
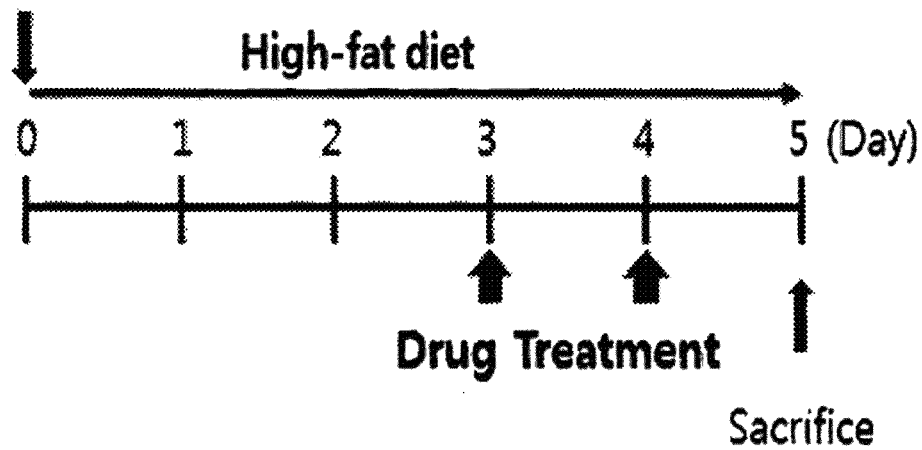
FIG. 11 illustrates the effects of JC1-40 and JC1-42 on the phosphorylation of AMPK and ACC and the expression of LXRα, SREBP-1, and FAS proteins in mice with high-fat diet-induced fatty liver.

Experimental Example 9: Effects of JC1-40 and JC1-42 on Phosphorylation of AMPK and ACC and Expression of LXRα, SREBP-1, and FAS Proteins in Mice with High-Fat Diet-Induced Fatty Liver As illustrated in FIG. 11a, six-week-old black laboratory mice were fed a high-fat diet containing safflower oil for 5 days. 3 days after the diet was fed, the mice were fed the high-fat diet containing safflower oil while being orally administered JC1-40 and JC1-42, which had been diluted with 0.5% carboxymethyl cellulose, at a dose of 10 mg/kg/day or 30 mg/kg/day for 2 days. 5 days after the diet was fed, the mice were sacrificed to extract liver tissues therefrom, and the expression of proteins was analyzed by western blotting analysis. That is, after treatment, each liver tissue was homogenized in a lysis buffer containing 50 mM NaCl, 50 mM Tris pH 7.4, 5 mM EDTA, 1% NP-40, and a protease inhibitor, and then centrifuged to obtain a total cell lysate. 20 μg to 30 μg of proteins collected from the total cell lysate was subjected to 7% to 9% SDS-PAGE, and was transferred to a polyvinylidene difluoride membrane (Millipore, Bedford, Mass., USA). The resulting product was subjected to blocking with 5% or 10% (w/v) nonfat dry milk in PBS containing 0.1% Tween-20, and was reacted with antibodies specific to RORα (Affinity BioReagents), LXRα, SREBP-1, FAS (Santa Cruz Biotechnology), phospho-AMPK, phospho-ACC (Cell signaling), and α-tubulin (Calbiochem). Immunoreactive proteins were detected with Amersham ECL western blotting detection reagents using an HRP-conjugated secondary antibody (Zymed Lab). Protein concentrations were quantified by BCA (Pierce) analysis, and the expression of α-tubulin was monitored as a control. The results thereof are illustrated in FIG. 11b.

Figure 11B:
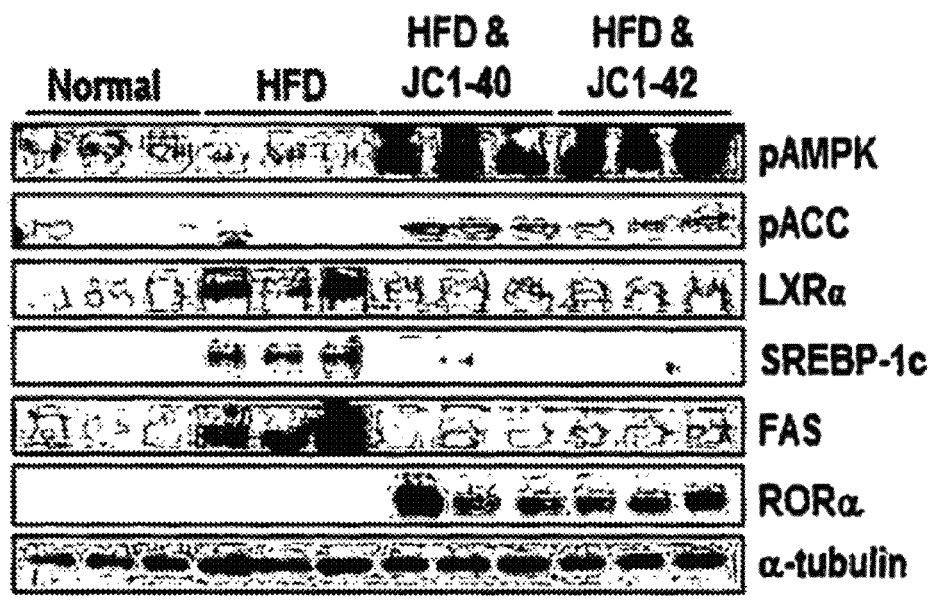

As illustrated in FIG. 11b, it was observed that the phosphorylation of AMPK and ACC was increased by JC1-40 and JC1-42, and that the expression of LXRα, SREBP-1, and FAS proteins, which had been increased by the high-fat diet, was decreased by JC1-40 and JC1-42.

Figure 12A:
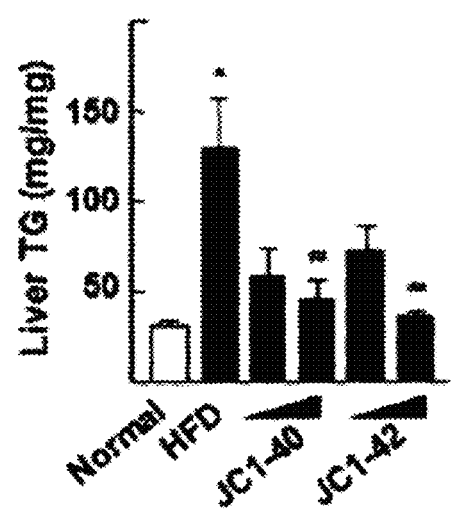
FIG. 12 illustrates the effects of JC1-40 and JC1-42 on intrahepatic triglyceride accumulation, intrahepatic fat accumulation, and changes in body weight in mice with high-fat diet-induced fatty liver.

Experimental Example 10. Effects of JC1-40 and JC1-42 on Intrahepatic Triglyceride Accumulation, Intrahepatic Fat Accumulation, and Changes in Body Weight in Mice with High-Fat Diet-Induced Fatty Liver As illustrated in FIG. 11a, six-week-old black laboratory mice were fed a high-fat diet containing safflower oil for 5 days. 3 days after the diet was fed, the mice were fed the high-fat diet containing safflower oil while being orally administered JC1-40 and JC142, which had been diluted with 0.5% carboxymethyl cellulose, at a dose of 10 mg/kg/day or 30 mg/kg/day for 2 days. 5 days after the diet was fed, the mice were sacrificed to extract liver tissues therefrom, and the amounts of intrahepatic triglycerides were measured using an EnzyChrom™ triglyceride assay kit (BioAssay Systems). As illustrated in FIG. 12a, it was observed that the amount of intrahepatic triglyceride, which had been increased by the high-fat diet, was decreased by JC1-40 and JC1-42.

Figure 12B:
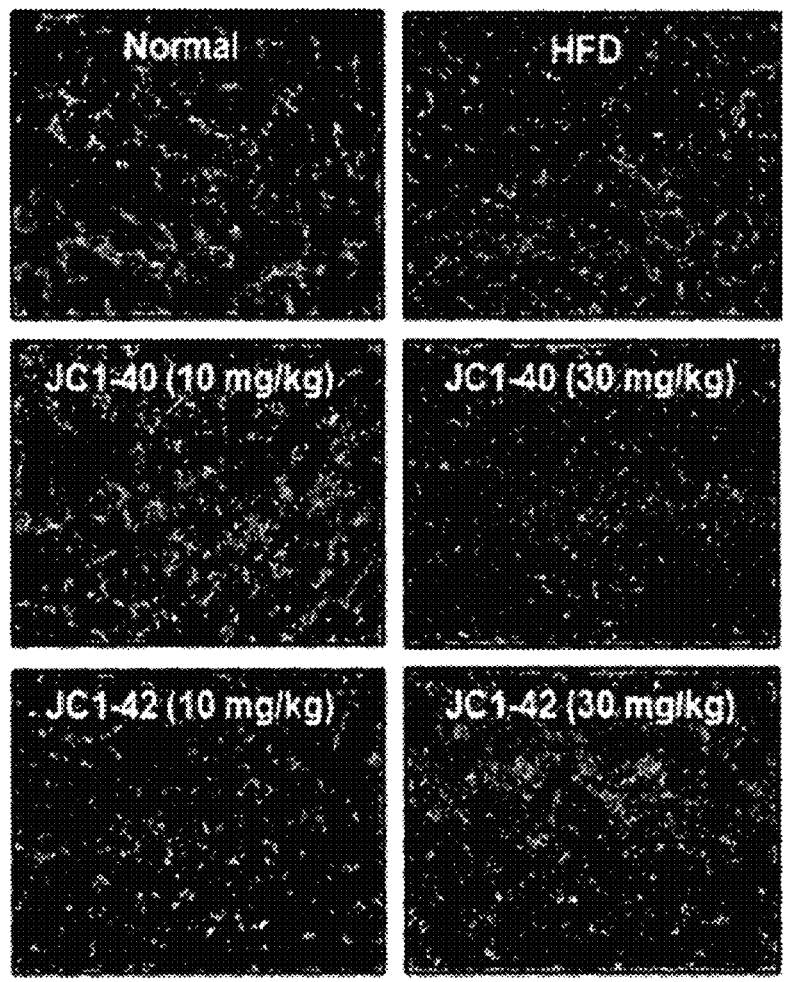

In addition, Oil Red O staining, which enables the identification of intrahepatic fat accumulation, was performed on the extracted liver tissues of the mice. As illustrated in FIG. 12b, it was observed that intrahepatic fat accumulation, which had been promoted by the high-fat diet, was decreased by JC1-40 and JC1-42.

Figure 12C:
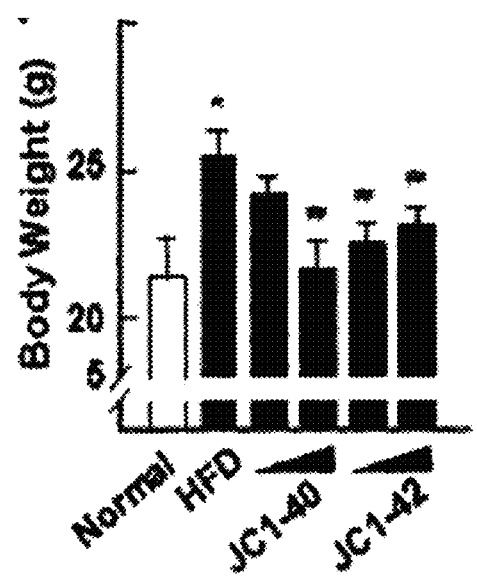

5 days after the high-fat diet was fed, the body weights of the mice were measured, and, as illustrated in FIG. 12c, it was observed that the body weights of the mice, which had been increased by the high-fat diet, were decreased by JC1-40 and JC1-42.

Experimental Example 11. Blood Biochemical Analysis by JC1-40 and JC1-42 in High-Fat Diet-Induced Fatty Liver Mice Model As illustrated in FIG. 11a, six-week-old black laboratory mice were fed a high-fat diet containing safflower oil for 5 days. 3 days after the diet was fed, the mice were fed the high-fat diet containing safflower oil while being orally administered JC1-40 and JC142, which had been diluted with 0.5% carboxymethyl cellulose, at a dose of 10 mg/kg/day or 30 mg/kg/day for 2 days. 5 days after the diet was fed, the mice were sacrificed to collect blood, and serum samples were collected therefrom.

Figure 13:
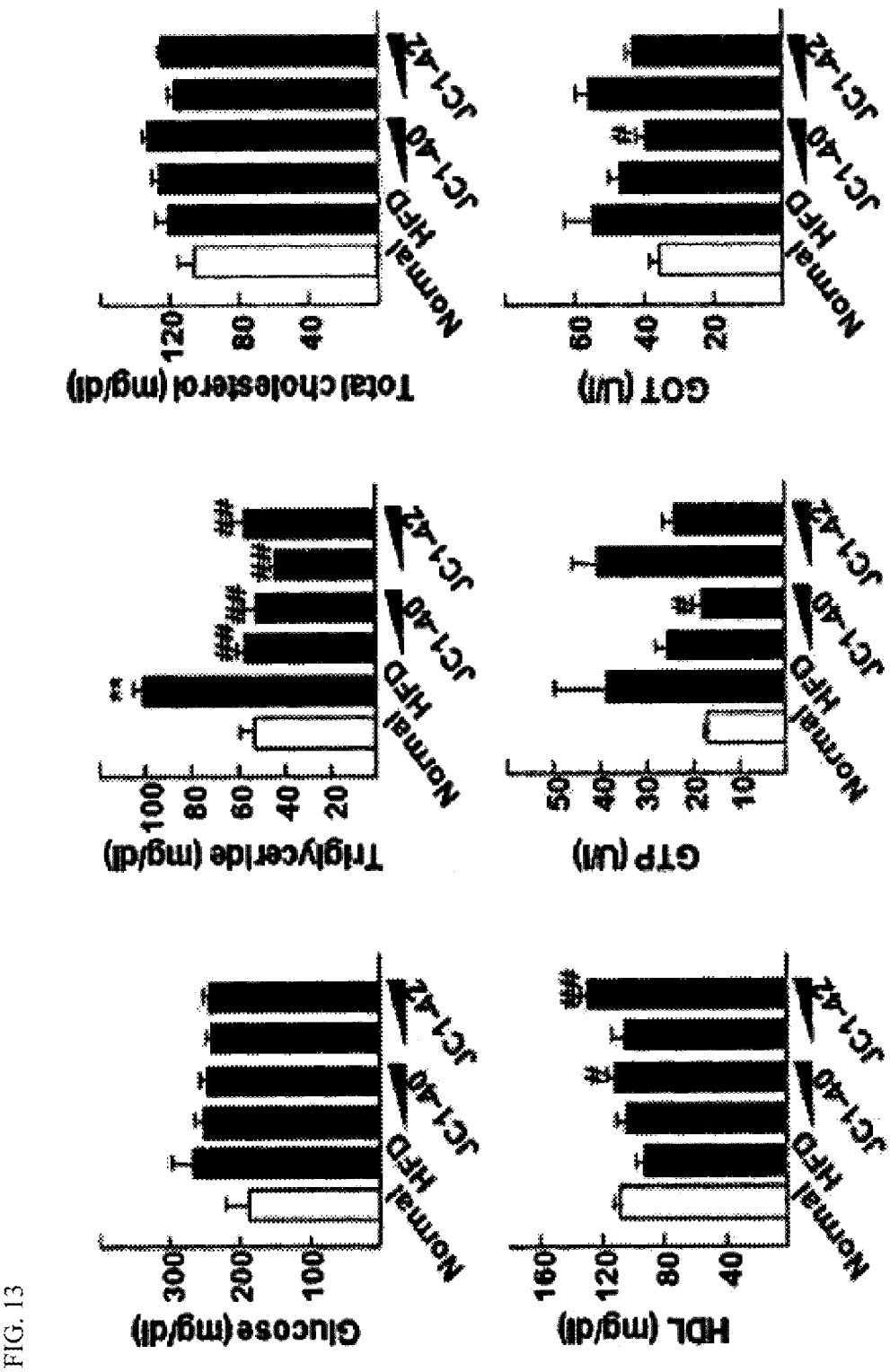
FIG. 13 illustrates blood biochemical analysis results for a high-fat diet-induced fatty liver mice model, showing the effects of JC1-40 and JC1-42.

As illustrated in FIG. 13, it was observed that the amounts of blood glucose and total blood cholesterol in the groups treated with JC1-40 and JC1-42 were not different from those in the high-fat diet group, but the amount of blood triglycerides, which had been increased by the high-fat diet, was decreased by JC1-40 and JC1-42. In addition, it was observed that the amount of high-density lipoproteins was increased in a group treated with JC1-40 and JC1-42 at a dose of 30 mg/kg/day compared to the high-fat diet group. It was observed that GPT and GOP, which represent liver function, were decreased in the group treated with JC1-40 at a dose of 30 mg/kg/day compared to the high-fat diet group.

Experimental Example 12. Effects of JC1-40 and JC1-42 on Proliferation of Vascular Smooth Muscle Cells A7r5, which is a rat smooth muscle cell line, was purchased from ATCC. A7r5 was cultured in 5% $CO_2$ using a DMEM supplemented with 10% FBS, penicillin (100 U/ml), and streptomycin (100 μg/ml) prior to use in an experiment. A7r5 cells ($2 \times 10^3$ cells/well) were seeded on a 96-well culture plate and cultured overnight. After culturing, the A7r5 cells were treated with each of the JC1-40 and JC1-42 compounds at a concentration of 100 μM for 2 days, 4 days, or 6 days. Subsequently, the A7r5 cells were treated with MTT (3-4,5-dimethylthiazol-2-yl)-2,5-diphenyl-tetrazolium bromide) (2 mg/ml, 50 μl) for 4 hours, and then the medium was removed and 200 μl of DMSO was added to the plate. The contents in the plate were mixed for 5 minutes, and then absorbance was measured at 595 nm. Data was attained as the mean and SD for the three independent experimental results, and the results thereof are illustrated in FIG. 14.

Figure 14:
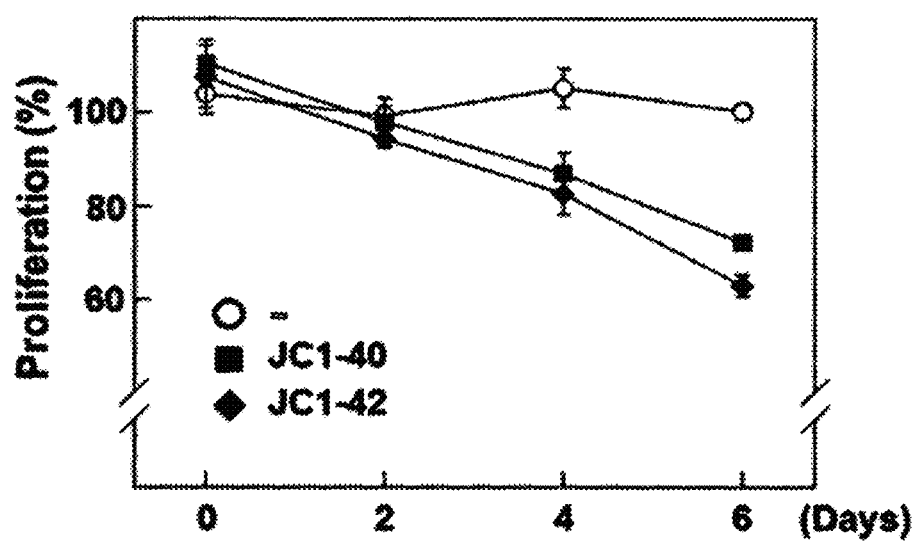
FIG. 14 illustrates the effects of JC1-40 and JC1-42 on the proliferation of vascular smooth muscle cells.

As illustrated in FIG. 14, it was observed that the proliferation of vascular smooth muscle cells was decreased by treatment with JC1-40 and JC1-42 (see FIG. 14).

Figure 15A:
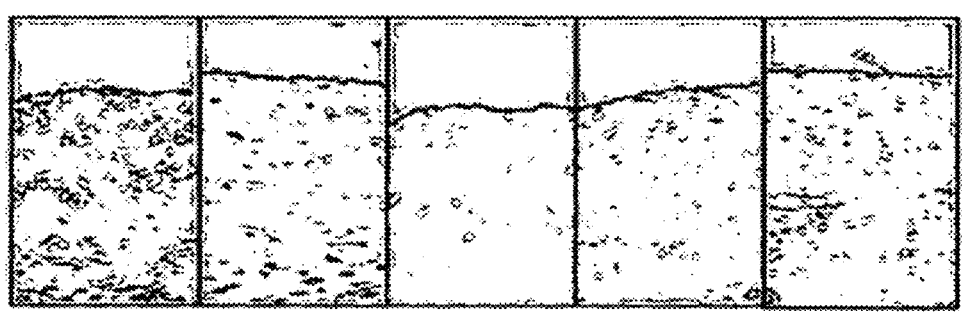
FIG. 15 illustrates the effect of JC1-40 on inner vascular proliferation after balloon dilatation.
Figure 15B:
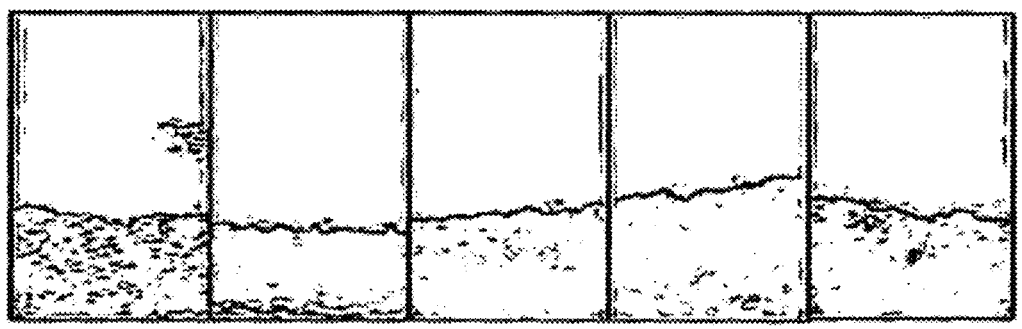

Experimental Example 13. Effect of JC1-40 on Inner Vascular Proliferation after Balloon Dilatation To verify the inhibition of angiostenosis by JC1-40, white mice were administered JC1-40 for days, followed by balloon dilatation and subsequent additional administration of JC1-40 for 14 days. An experimental group was orally administered JC1-40 at a dose of 5 mg/kg (in 0.5% carboxymethyl cellulose, 2 ml/kg) (n=5), and a control was orally administered 0.5% carboxymethylcellulose at a dose of 2 mg/kg (n=5). The balloon dilatation was performed as follows. The cervical portion of each with mouse was incised to expose a common carotid artery, and the internal branch was tied at a site where the common carotid artery branches into the external branch and the internal branch. The external branch was partially incised, and then ballooning was performed three times with a 2F Fogarty balloon catheter to damage blood vessels. Subsequently, the balloon catheter was removed, and the incision site was tied. After balloon dilatation, the white mice were administered the drug for 14 days and then sacrificed to cut the site in artery that included the damaged region. The obtained blood vessels of each of the JC1-40 experimental group and the control were sectioned, the inner vascular layer thereof was subjected to Hematoxylin and Eosin (H&E) staining, and then the effect of JC1-40 on the inhibition of inner vascular proliferation was examined, and the results thereof are illustrated in FIG. 15. FIG. 15*a* illustrates cross-sections of blood vessels of the control, and FIG. 15*b* illustrates cross-sections of blood vessels of the experimental group administered JC1-40.

As illustrated in FIG. 15, it was observed that the proliferation of the inner vascular layer by balloon dilatation was inhibited by the administration of JC1-40 (see FIG. 15).

From the results of Experimental Examples 12 and 13, novel compounds activating the RORα gene, e.g., the JC1 compounds, are expected to be applicable to the inhibition of formation of atherosclerotic plaques accompanied by vascular smooth muscle proliferation and the prevention of vascular restenosis caused by vascular smooth muscle proliferation after a balloon therapy or stenting.

Experimental Example 14. Improvement in Alcoholic Fatty Acid Mice Model Caused by JC1-40

Eight-week-old black male laboratory mice (C57BL/6) were divided into: 1) control (n=8); 2) JC1-40-administered control (n=8); 3) alcohol group (n=12); and 4) JC1-40-administered alcohol group (n=12), and fed a Lieber-DeCarli liquid diet (Dyets Inc, Bethlehem, Pa., USA). The Lieber-DeCarli liquid diet in the form of powder was purchased, and then water was added thereto every morning to form a liquid-type feed such that 1 ml of the feed contained 1 kcal. The alcohol group was fed a gradually increasing amount of alcohol with an increment of 0.5% during a 2-week adaptation period, and then was fed a feed containing 5% alcohol for 5 weeks. The feed of the control included maltose dextrin instead of alcohol, and for pair-feeding, the feed included maltose dextrin in an amount providing the same calories as the calories that the amount of the feed fed to the mice of the alcohol group contained. During the 5-week ingestion of 5% alcohol, JC1-40 diluted with 0.5% carboxymethyl cellulose was orally administered once a day at a dose of 10 mg/kg body weight for 2 weeks prior to sacrificing the mice. After the 5-week alcohol feeding period was completed, the mice were fasted for 12 hours, and anesthetized to incise the abdomen, and blood and liver were removed from each mouse.

Figure 16A:
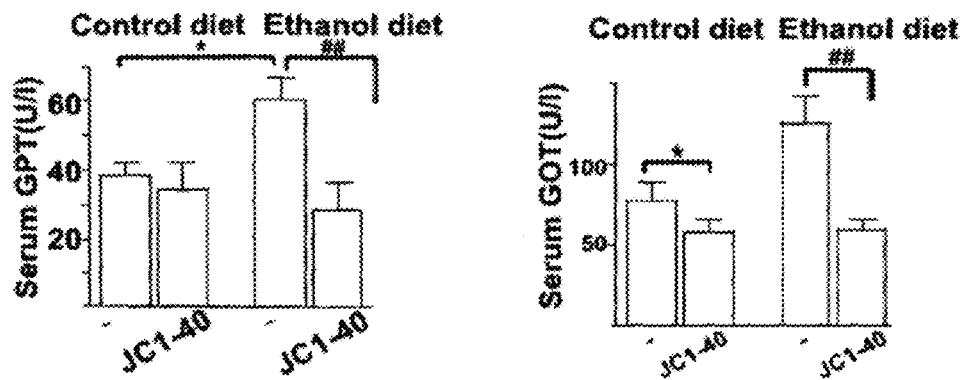
FIG. 16 illustrates improvement in an alcoholic fatty liver mice model caused by JC1-40.
Figure 16B:
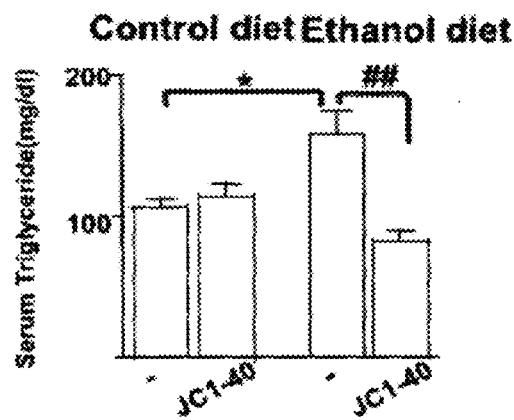
Figure 16C:
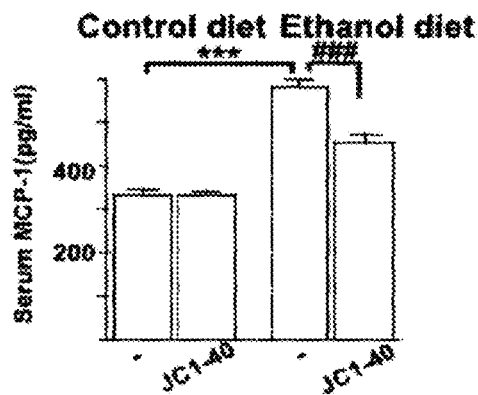
Figure 16D:
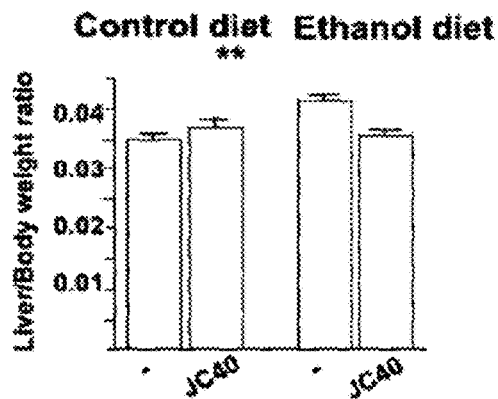
Figure 16E:
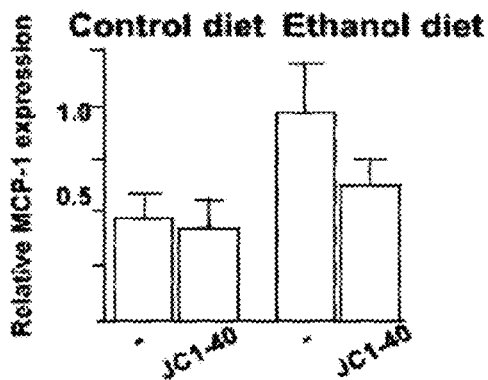
Figure 16F:
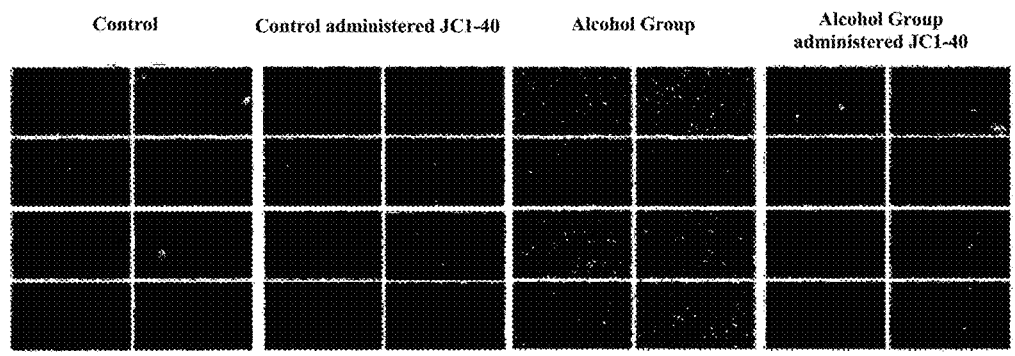

As illustrated in FIG. 16*a*, as a result of measuring GPT and GOT in plasma separated from blood to measure liver damage, it was confirmed that the alcohol group exhibited significant increases of GPT and GOP as much as about 50% compared to the control, and the JC1-40-treated alcohol group exhibited decreases in GPT and GOT to levels of the control. As illustrated in FIGS. 16*b* and 16*c*, when the levels of blood triglycerides and cytokine MCP-1 were measured by ELISA, it was observed that the levels were significantly decreased in the JC1-40-treated alcohol group, unlike in the alcohol group in which the levels were increased. As illustrated in FIG. 16*d*, when the weight percentage of liver in body was determined by dividing the weight of liver by the body weight of each mouse, it was confirmed that the percentage of liver, which had increased due to alcohol ingestion, decreased with high significance due to the administration of JC1-40. As illustrated in FIG. 16*e*, when the expression of the MCP-1 protein was analyzed through western blotting analysis, the expression of MCP-1, which had increased in the alcohol group, decreased to the level of the control due to the administration of JC1-40. When morphological changes in liver tissue was examined through tissue staining (Hematoxyllin & Eosin), it was observed that the accumulation of alcohol-induced lipid vesicles was significantly reduced by JC1-40 administration (see FIG. 16*f*).

The foregoing description of the present invention is provided for illustrative purposes only, and it will be understood by those of ordinary skill in the art to which the present invention pertains that the present invention may be easily modified in other particular forms without changing the technical spirit or essential characteristics of the present invention. Thus, the above-described examples and experimental examples should be construed as being provided for illustrative purposes only and not for purposes of limitation.

INDUSTRIAL APPLICABILITY

The present invention is expected to be effective in the treatment and prevention of metabolic diseases and inflammatory diseases and useful particularly for the prevention and treatment of liver diseases through the regulation of homeostasis of cholesterol and the inhibition of lipid synthesis.

Sequence Listing Free Text

<110> SNU R & DB FOUNDATION

<120> New Thiourea derivatives as RORa Activators, and pharmaceutical compositions containing the same

<130> PCT01471

<150> 1020110048455
<151> 2011-05-23

<150> 1020110128903
<151> 2011-12-05

<150> 1020120054540
<151> 2012-05-23

<160> 20

<170> KopatentIn 2.0

<210> 1
<211> 22
<212> DNA
<213> Artificial Sequence

<220>

<223> MCAD primer sequence (forward)

<400> 1
ctaccaagta tgccctggaa ag                    22

<210> 2
<211> 22
<212> DNA
<213> Artificial Sequence

<220>

<223> MCAD primer sequence (reverse)

<400> 2
tgtgttcacg ggctacaata ag                    22

<210> 3
<211> 21
<212> DNA
<213> Artificial Sequence

<220>

<223> ACO1 primer sequence (forward)

<400> 3
gggcatggct attctcattg c                     21

<210> 4
<211> 26
<212> DNA
<213> Artificial Sequence

<220>

<223> ACO1 primer sequence (reverse)

<400> 4
cgaacaaggt caacagaagt taggtt                26

<210> 5
<211> 21
<212> DNA
<213> Artificial Sequence

<220>

<223> ACO2 primer sequence (forward)

<400> 5
gcggacatgg ctactcaaag c                     21

<210> 6
<211> 21
<212> DNA
<213> Artificial Sequence

<220>

<223> ACO2 primer sequence (reverse)

<400> 6
gcagtgcacc ttagcagcct g                     21

<210> 7
<211> 22
<212> DNA
<213> Artificial Sequence

<220>

<223> HMGCS2 primer sequence (forward)

<400> 7
ggaacccata tggagaatgt gt                    22

<210> 8
<211> 22
<212> DNA
<213> Artificial Sequence

<220>

<223> HMGCS2 primer sequence (reverse)

<400> 8
tcctgagagg cctttagaag tg                    22

<210> 9
<211> 23
<212> DNA
<213> Artificial Sequence

<220>

<223> CPT1 primer sequence (forward)

<400> 9
agacggtgga acagaggctg aag                   23

<210> 10
<211> 27
<212> DNA
<213> Artificial Sequence

<220>

<223> CPT1 primer sequence (reverse)

<400> 10
tgagaccaaa caaagtgatg atgtcag                27

<210> 11
<211> 19
<212> DNA
<213> Artificial Sequence

<220>

Sequence Listing Free Text

<223> ACS primer sequence (forward)

<400> 11
agcagagctt cgcagcggc                    19

<210> 12
<211> 21
<212> DNA
<213> Artificial Sequence

<220>

<223> ACS primer sequence (reverse)

<400> 12
tctgctgttt tcgctgggtc c                 21

<210> 13
<211> 21
<212> DNA
<213> Artificial Sequence

<220>

<223> B-actin primer sequence (forward)

<400> 13
cgtgggccgc cctaggcacc a                 21

<210> 14
<211> 21
<212> DNA
<213> Artificial Sequence

<220>

<223> B-actin primer sequence (reverse)

<400> 14
ttggcttagg gttcaggggg g                 21

<210> 15
<211> 19
<212> DNA
<213> Artificial Sequence

<220>

<223> CD36 primer sequence (forward)

<400> 15
ggaactgtgg gctcattgc                    19

<210> 16
<211> 21
<212> DNA
<213> Artificial Sequence

<220>

<223> CD36 primer sequence (reverse)

<400> 16
catgagaatg cctccaaaca c                 21

<210> 17
<211> 18
<212> DNA
<213> Artificial Sequence

<220>

<223> MTTP primer sequence (forward)

<400> 17
ccttcattca gcacctca                     18

<210> 18
<211> 18
<212> DNA
<213> Artificial Sequence

<220>

<223> MTTP primer sequence (reverse)

<400> 18
tgacaagtgt cccagtga                     18

<210> 19
<211> 20
<212> DNA
<213> Artificial Sequence

<220>

<223> ApoB100 primer sequence (forward)

<400> 19
taaatggagc acttttcaag               20

<210> 20
<211> 18
<212> DNA
<213> Artificial Sequence

<220>

<223> ApoB100 primer sequence (reverse)

<400> 20
ggaacagcag cagtagcg                     18

---

SEQUENCE LISTING

<160> NUMBER OF SEQ ID NOS: 20

<210> SEQ ID NO 1
<211> LENGTH: 22
<212> TYPE: DNA
<213> ORGANISM: Artificial Sequence
<220> FEATURE:
<223> OTHER INFORMATION: MCAD primer seqeunce(forward)

<400> SEQUENCE: 1
ctaccaagta tgccctggaa ag                22

```
<210> SEQ ID NO 2
<211> LENGTH: 22
<212> TYPE: DNA
<213> ORGANISM: Artificial Sequence
<220> FEATURE:
<223> OTHER INFORMATION: MCAD primer seqeunce(reverse)

<400> SEQUENCE: 2
tgtgttcacg ggctacaata ag                                        22

<210> SEQ ID NO 3
<211> LENGTH: 21
<212> TYPE: DNA
<213> ORGANISM: Artificial Sequence
<220> FEATURE:
<223> OTHER INFORMATION: ACO1 primer seqeunce(forward)

<400> SEQUENCE: 3
gggcatggct attctcattg c                                         21

<210> SEQ ID NO 4
<211> LENGTH: 26
<212> TYPE: DNA
<213> ORGANISM: Artificial Sequence
<220> FEATURE:
<223> OTHER INFORMATION: ACO1 primer seqeunce(reverse)

<400> SEQUENCE: 4
cgaacaaggt caacagaagt taggtt                                    26

<210> SEQ ID NO 5
<211> LENGTH: 21
<212> TYPE: DNA
<213> ORGANISM: Artificial Sequence
<220> FEATURE:
<223> OTHER INFORMATION: ACO2 primer seqeunce(forward)

<400> SEQUENCE: 5
gcggacatgg ctactcaaag c                                         21

<210> SEQ ID NO 6
<211> LENGTH: 21
<212> TYPE: DNA
<213> ORGANISM: Artificial Sequence
<220> FEATURE:
<223> OTHER INFORMATION: ACO2 primer seqeunce(reverse)

<400> SEQUENCE: 6
gcagtgcacc ttagcagcct g                                         21

<210> SEQ ID NO 7
<211> LENGTH: 22
<212> TYPE: DNA
<213> ORGANISM: Artificial Sequence
<220> FEATURE:
<223> OTHER INFORMATION: HMGCS2 primer seqeunce(forward)

<400> SEQUENCE: 7
ggaacccata tggagaatgt gt                                        22

<210> SEQ ID NO 8
<211> LENGTH: 22
<212> TYPE: DNA
<213> ORGANISM: Artificial Sequence
<220> FEATURE:
<223> OTHER INFORMATION: HMGCS2 primer seqeunce(reverse)
```

```
<400> SEQUENCE: 8
tcctgagagg cctttagaag tg                                              22

<210> SEQ ID NO 9
<211> LENGTH: 23
<212> TYPE: DNA
<213> ORGANISM: Artificial Sequence
<220> FEATURE:
<223> OTHER INFORMATION: CPT1 primer seqeunce(forward)

<400> SEQUENCE: 9
agacggtgga acagaggctg aag                                             23

<210> SEQ ID NO 10
<211> LENGTH: 27
<212> TYPE: DNA
<213> ORGANISM: Artificial Sequence
<220> FEATURE:
<223> OTHER INFORMATION: CPT1 primer seqeunce(reverse)

<400> SEQUENCE: 10
tgagaccaaa caaagtgatg atgtcag                                         27

<210> SEQ ID NO 11
<211> LENGTH: 19
<212> TYPE: DNA
<213> ORGANISM: Artificial Sequence
<220> FEATURE:
<223> OTHER INFORMATION: ACS primer seqeunce(forward)

<400> SEQUENCE: 11
agcagagctt cgcagcggc                                                  19

<210> SEQ ID NO 12
<211> LENGTH: 21
<212> TYPE: DNA
<213> ORGANISM: Artificial Sequence
<220> FEATURE:
<223> OTHER INFORMATION: ACS primer seqeunce(reverse)

<400> SEQUENCE: 12
tctgctgttt tcgctgggtc c                                               21

<210> SEQ ID NO 13
<211> LENGTH: 21
<212> TYPE: DNA
<213> ORGANISM: Artificial Sequence
<220> FEATURE:
<223> OTHER INFORMATION: B-actin primer seqeunce(forward)

<400> SEQUENCE: 13
cgtgggccgc cctaggcacc a                                               21

<210> SEQ ID NO 14
<211> LENGTH: 21
<212> TYPE: DNA
<213> ORGANISM: Artificial Sequence
<220> FEATURE:
<223> OTHER INFORMATION: B-actin primer seqeunce(reverse)

<400> SEQUENCE: 14
ttggcttagg gttcaggggg g                                               21

<210> SEQ ID NO 15
<211> LENGTH: 19
```

```
<212> TYPE: DNA
<213> ORGANISM: Artificial Sequence
<220> FEATURE:
<223> OTHER INFORMATION: CD36 primer seqeunce(forward)

<400> SEQUENCE: 15
ggaactgtgg gctcattgc                                              19

<210> SEQ ID NO 16
<211> LENGTH: 21
<212> TYPE: DNA
<213> ORGANISM: Artificial Sequence
<220> FEATURE:
<223> OTHER INFORMATION: CD36 primer seqeunce(reverse)

<400> SEQUENCE: 16
catgagaatg cctccaaaca c                                           21

<210> SEQ ID NO 17
<211> LENGTH: 18
<212> TYPE: DNA
<213> ORGANISM: Artificial Sequence
<220> FEATURE:
<223> OTHER INFORMATION: MTTP primer seqeunce(forward)

<400> SEQUENCE: 17
ccttcattca gcacctca                                               18

<210> SEQ ID NO 18
<211> LENGTH: 18
<212> TYPE: DNA
<213> ORGANISM: Artificial Sequence
<220> FEATURE:
<223> OTHER INFORMATION: MTTP primer seqeunce(reverse)

<400> SEQUENCE: 18
tgacaagtgt cccagtga                                               18

<210> SEQ ID NO 19
<211> LENGTH: 20
<212> TYPE: DNA
<213> ORGANISM: Artificial Sequence
<220> FEATURE:
<223> OTHER INFORMATION: ApoB100 primer seqeunce(forward)

<400> SEQUENCE: 19
taaatggagc acttttcaag                                             20

<210> SEQ ID NO 20
<211> LENGTH: 18
<212> TYPE: DNA
<213> ORGANISM: Artificial Sequence
<220> FEATURE:
<223> OTHER INFORMATION: ApoB100 primer seqeunce(reverse)

<400> SEQUENCE: 20
ggaacagcag cagtagcg                                               18
```

The invention claimed is:

1. A compound represented by Formula (I) below or a pharmaceutically acceptable salt thereof:

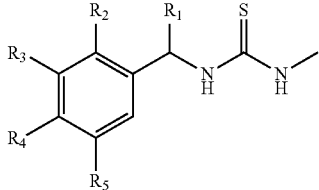

Formula (I)

wherein:
R₁ is a hydrogen atom or a C₁-C₃ alkyl group;
R₂ is a hydrogen atom, a halogen atom, a C₁-C₃ alkyl group, a C₁-C₃ alkoxy group, a nitro group, a hydroxyl group, or a phenoxy group;
R₃ is a hydrogen atom, a halogen atom, a C₁-C₃ alkyl group, a C₁-C₃ alkoxy group, a nitro group, a hydroxyl group, or a phenoxy group;
R₄ is a nitro group, a cyano group, a dimethylamino group, a methylsulfonylamide group, a trifluoromethyl group, a vinyl benzene group, a phenoxy group, a benzoxy group, an aryl group, or a phenylamine group, wherein in the case where R₄ is an aryl group or a phenoxy group, the aromatic moiety of the aryl or phenoxy group may be substituted with a C₁-C₃ alkyl group, a C₁-C₃ alkoxy group, a trifluoromethyl group, or a t-butyl group; and R₄ may link to R₃ to form a ring; and
R₅ is a hydrogen atom, a halogen atom, a C₁-C₃ alkyl group, a C₁-C₃ alkoxy group, a nitro group, a hydroxyl group, or a phenoxy group.

2. The compound of claim 1, wherein R₄ is an aryl group or a phenoxy group and the aromatic ring thereof is substituted with a C₁-C₃ alkyl group, a C₁-C₃ alkoxy group, a trifluoromethyl group, or a t-butyl group.

3. The compound of claim 1, wherein R₃ and R₄ are linked to each other to form a ring.

4. The compound of claim 1, wherein not all of R₂ to R₅ are hydrogen at the same time.

5. A lipid accumulation inhibitor composition comprising the compound of claim 1 or a pharmaceutically acceptable salt thereof as an active ingredient.

6. A method of treating a metabolic disease, comprising administering a composition comprising an effective amount of a compound represented by Formula (I) below or a pharmaceutically acceptable salt thereof:

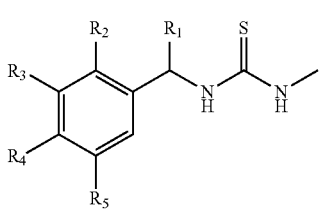

Formula (I)

wherein:
R₁ is a hydrogen atom or a C₁-C₃ alkyl group;
R₂ is a hydrogen atom, a halogen atom, a C₁-C₃ alkyl group, a C₁-C₃ alkoxy group, a nitro group, a hydroxyl group, or a phenoxy group;
R₃ is a hydrogen atom, a halogen atom, a C₁-C₃ alkyl group, a C₁-C₃ alkoxy group, a nitro group, a hydroxyl group, or a phenoxy group;
R₄ is a hydrogen atom, a halogen atom, a C₁-C₃ alkyl group, a C₁-C₃ alkoxy group, a nitro group, a hydroxyl group, a cyano group, a dimethylamino group, a methylsulfonylamide group, a trifluoromethyl group, a vinyl benzene group, a phenoxy group, a benzoxy group, an aryl group, or a phenylamine group, wherein in the case where R₄ is an aryl group or a phenoxy group, the aromatic moiety of the aryl or phenoxy group may be substituted with a C₁-C₃ alkyl group, a C₁-C₃ alkoxy group, a trifluoromethyl group, or a t-butyl group, and R₃ and R₄ may link together to form a ring; and
R₅ is a hydrogen atom, a halogen atom, a C₁-C₃ alkyl group, a C₁-C₃ alkoxy group, a nitro group, a hydroxyl group, or a phenoxy group.

7. The method of claim 6, wherein the metabolic disease is arteriosclerosis.

8. The method of claim 6, wherein the metabolic disease is hyperlipidemia or fatty liver.

9. The method of claim 6, wherein the metabolic disease is alcoholic fatty liver.

10. A compound selected from the group consisting of:
1-(benzo[1,3]dioxyl-5-methyl)-3-methyl-thiourea (JC1-8)
1-(4-dimethylamino-benzyl)-3-methyl-thiourea (JC1-10)
1-(4-trifluoromethyl-benzyl)-3-methyl-thiourea (JC1-11)
1-(4-nitro-benzyl)-3-methyl-thiourea (JC1-12)
1-(4-t-butyl-benzyl)-3-methyl-thiourea (JC1-13)
1-(2-ethoxy-benzyl)-3-methyl-thiourea (JC1-16)
1-(3-nitro-benzyl)-3-methyl-thiourea (JC1-17)
1-(2-nitro-benzyl)-3-methyl-thiourea (JC1-18)
1-(4-phenyl-benzyl)-3-methyl-thiourea (JC1-24)
1-(4-cyano-benzyl)-3-methyl-thiourea (JC1-26)
R-(+)-1-[1-(4-methoxy-phenyl)-ethyl]-3-methyl-thiourea (JC1-35)
S-(−)-1-[1-(4-methoxy-phenyl)-ethyl]-3-methyl-thiourea (JC1-36)
N-4-[(3-methyl-thioureido)-methyl]-phenyl-methanesulfonamide (JC1-37)
1-methyl-3-(4-pyridinyl-2-benzyl)-thiourea (JC1-38)
1-(2-allyloxy-benzyl)-3-methyl-thiourea (JC1-39)
1-(4-benzyloxy-benzyl)-3-methyl-thiourea (JC1-40)
1-(3-benzyloxy-4-methoxy-benzyl)-3-methyl-thiourea (JC1-41)
1-(4-phenoxy-benzyl)-3-methyl-thiourea (JC1-42)
1-methyl-3-naphthalene-2-methyl-thiourea (JC1-43)
1-(3-ethoxy-biphenyl-4-methyl)-3-methyl-thiourea (JC1-44)
1-(4'-tert-butyl-3-ethoxy-biphenyl-4-methyl)-thiourea (JC1-45)
1-(3,3'-diethoxy-biphenyl-4-methyl)-3-methyl-thiourea (JC1-46)
1-(2-ethoxy-4-styryl-benzyl)-3-methyl-thiourea (JC1-47)
1-(3-ethoxy-4'-trifluoromethyl-biphenyl-4-methyl)-3-methyl-thiourea (JC1-48)
1-methyl-3-(3-phenoxy-benzyl)-thiourea (JC1-50)
1-methyl-3-(2-phenoxy-benzyl)-thiourea (JC1-51)
1-[4-(4-fluoro-phenoxy)-benzyl]-3-methyl-thiourea (JC1-52)
1-[4-(4-methoxy-phenoxy)-benzyl]-3-methyl-thiourea (JC1-53).

* * * * *